US012636615B2

(12) United States Patent
Zydney et al.

(10) Patent No.: US 12,636,615 B2
(45) Date of Patent: May 26, 2026

(54) SEPARATION APPARATUS AND METHOD

(71) Applicant: THE PENN STATE RESEARCH FOUNDATION, University Park, PA (US)

(72) Inventors: Andrew Lawrence Zydney, University Park, PA (US); Christopher J. Yehl, University Park, PA (US)

(73) Assignee: The Penn State Research Foundation, University Park, PA (US)

( * ) Notice: Subject to any disclaimer, the term of this patent is extended or adjusted under 35 U.S.C. 154(b) by 336 days.

(21) Appl. No.: 18/262,989

(22) PCT Filed: Aug. 30, 2021

(86) PCT No.: PCT/US2021/048183
§ 371 (c)(1),
(2) Date: Jul. 26, 2023

(87) PCT Pub. No.: WO2022/182388
PCT Pub. Date: Sep. 1, 2022

(65) Prior Publication Data
US 2024/0101597 A1     Mar. 28, 2024

Related U.S. Application Data

(60) Provisional application No. 63/225,712, filed on Jul. 26, 2021, provisional application No. 63/154,296, filed on Feb. 26, 2021.

(51) Int. Cl.
*B01D 61/16* (2006.01)
*B01D 61/18* (2006.01)
(Continued)

(52) U.S. Cl.
CPC ........... *B01D 61/243* (2013.01); *B01D 61/16* (2013.01); *B01D 61/18* (2013.01); *B01D 61/58* (2013.01);
(Continued)

(58) Field of Classification Search
CPC ...... B01D 61/16; B01D 61/18; B01D 61/243; B01D 61/58; B01D 63/02; C07K 1/34;
(Continued)

(56) References Cited

U.S. PATENT DOCUMENTS 6,146,902 A     11/2000  McMaster
7,497,950 B2     3/2009  Sirkar et al.
(Continued)

OTHER PUBLICATIONS

International Search Report for PCT/US2021/048183 dated Dec. 2, 2021.
(Continued)

*Primary Examiner* — John Kim
(74) *Attorney, Agent, or Firm* — Buchanan Ingersoll & Rooney PC

(57) ABSTRACT

Protein separation can be provided based on a High Performance Countercurrent Membrane Purification (HPCMP), which can exploit highly selective diffusive transport across thin walls of a hollow fiber membrane for separation of proteins. Embodiments of an HPCMP system can separate mixtures of multiple proteins (e.g. separate BSA and Mb) or other biological material and provide high yields (e.g. achieving greater than 98% yield of both proteins with purification factors greater than 100-fold, etc.). Embodiments of a HPCMP system can be configured for high resolution separations in the preparation of biopharmaceuticals and natural protein products. Other embodiments can be utilized in other protein separation environments or biological material separation environments.

21 Claims, 21 Drawing Sheets

(51) Int. Cl.

| | |
|---|---|
| *B01D 61/24* | (2006.01) |
| *B01D 61/58* | (2006.01) |
| *B01D 63/02* | (2006.01) |
| *C07K 1/34* | (2006.01) |
| *C07K 14/765* | (2006.01) |
| *C07K 14/805* | (2006.01) |
| *C07K 16/28* | (2006.01) |

(52) U.S. Cl.
CPC ................ *B01D 63/02* (2013.01); *C07K 1/34* (2013.01); *C07K 14/765* (2013.01); *C07K 14/805* (2013.01); *C07K 16/2803* (2013.01)

(58) Field of Classification Search
CPC . C07K 14/765; C07K 14/805; C07K 16/2803
See application file for complete search history.

(56) References Cited

U.S. PATENT DOCUMENTS

| | | | |
|---|---|---|---|
| 10,421,042 B2 | 9/2019 | Schwan et al. | |
| 2005/0255227 A1* | 11/2005 | Sirkar ..................... | C07K 1/34 |
| | | | 426/656 |
| 2017/0056825 A1* | 3/2017 | Schwan ................ | C12M 47/10 |

OTHER PUBLICATIONS

Written Opinion of the International Searching Authority for PCT/US2021/048183 dated Dec. 2, 2021.
SARASWAT Mayank et al. Preparative purification of recombinant proteins: current status and future trends. BioMed Research International, vol. 2013, Article ID 312709, p. 18, http://dx.doi.org/10.1155/2013/312709.

* cited by examiner

Sieving Coefficient
and Fractional
Removal Value

Dextran Molecular Weight, MW (kDa)

Myoglobin
Concentration
(mg/L)

HPTFF Time (min)

Myoglobin
Concentration
(mg/L)

HPTFF Time (min)

RI Detector
(nRIU)

Draw x20

Elution Time (min)

RI Detector
(nRIU)

Elution Time (min)

RI Detector
(nRIU)

Elution Time (min)

Myoglobin
Impurity Removal
(%)

Yield, $Y_1$

Yield, $Y_2$

Purification Factor, $P_2$

Selectivity, $\psi$

Mean Pore Radius (nm)

Yield in
Draw t.mod = 7.75 hr

1xPBS 150mM pH = 7.8 t.mod = 8 hr

NaCH3COO 150mM pH = 5.2 t.mod = 8 hr

NaCH3COO 150mM pH = 5.2

SEPARATION APPARATUS AND METHOD

CROSS-REFERENCE TO RELATED APPLICATIONS

The present application is the U.S. national stage application of International Patent Application No. PCT/US2021/048183, which claims priority to U.S. Provisional Patent Application No. 63/154,296, which was filed on Feb. 26, 2021, and to U.S. Provisional Patent Application No. 63/225,712, which was filed on Jul. 26, 2021. The entirety of International Patent Application No. PCT/US2021/048183 and U.S. Provisional Patent Application Nos. 63/154,296 and 63/225,712 is are incorporated by reference herein.

BACKGROUND

Tangential Flow Filtration (TFF), also referred to as crossflow filtration, is used in the commercial scale manufacture of essentially all biotherapeutics. This includes the use of tangential flow microfiltration for initial clarification of cell culture fluid as well as ultrafiltration for final concentration and formulation. TFF operates with the feed flowing parallel to the filtering membrane and perpendicular to the direction of the filtrate flow. These TFF processes typically involve systems in which there are relatively large differences in size, e.g., between cells/cell debris (typically 0.1-10 μm in size) and proteins (≈10 nm) or between proteins and buffer components (≤1 nm). Examples of a TFF system are disclosed in U.S. Pat. Nos. 10,934,325 and 4,888,155, U.S. Pat. App. Pub. No. 2020/0139303, and International Publication No. WO 2019/236811.

High Performance Tangential Flow Filtration or HPTFF can provide highly selective separations by operating the pressure-driven TFF device in the pressure-dependent regime, i.e., at or below the "transition point" in a plot of filtrate flux as a function of transmembrane pressure. HPTFF has been demonstrated in small-scale laboratory systems for the purification of an antigen binding fragment from *E. coli* host cell proteins, a monoclonal antibody from mammalian cell host proteins, and a pegylated product from residual protein and polyethylene glycol (PEG) after the conjugation reaction. Examples of HPTFF systems are disclosed in U.S. Pat. App. Pub. No. 2005/0197496 and U.S. Pat. Nos. 7,153, 426, 6,926,833 and 5,490,937.

SUMMARY

Despite the interest in HPTFF systems, there is still a lack of commercially available charged ultrafiltration membranes suitable for high resolution protein separations. HPTFF systems also experience challenges with membrane fouling associated with the pressure-driven filtration and have difficulty in obtaining sufficient selectivity between similarly-sized products and impurities. HPTFF systems also often require large buffer consumption to be utilized for the diafiltration process. In addition, HPTFF is performed as a batch process using fairly expensive membrane modules.

We determined that embodiments of our high performance countercurrent membrane purification system and method can provide significant improvements as compared to conventional HPTFF and TFF systems by providing high yield separation while reducing the operational cost and capital cost for such systems. In some embodiments, the separation system can utilize a low-cost hollow fiber membrane to provide continuous high performance countercurrent membrane purification (HPCMP). Methods can utilize embodiments of such systems. Embodiments can be configured so that single use membranes can be utilized (e.g. used once and, after the membrane life has been used, the membrane is replaced with a new single use membrane). It is contemplated, however, that other embodiments may utilize membranes that can be regenerated for re-use. In some embodiments, there may be multiple membrane units that can operate in parallel so that while one membrane is off-line to undergo regeneration or replacement, one or more other membranes may be online to perform protein separation. Other embodiments may utilize membrane in series, e.g., to achieve purification of more complex protein mixtures, or in another type of flow arrangement.

In contrast to HPTFF, embodiments of our HPCMP system and method can be configured as a fully continuous, diffusion-driven membrane process that can be performed with low-cost commercially available hollow fiber membranes for long operational times with no detectable fouling and with relatively low buffer consumption. Embodiments can be configured for blood purification, monoclonal antibody purification, or other protein separation environments. Our HPCMP system can also be used for removal of non-protein impurities, e.g., excess PEG, in the purification of pegylated protein products.

In some embodiments, HPCMP can be used for initial purification to remove host cell proteins from a protein product. This continuous process can provide a platform for utilization as part of a continuous downstream process (e.g., combined with additional polishing operations and final formulation) for purification of high-value biotherapeutics like monoclonal antibodies, etc. The use of HPCMP in such embodiments can be configured to remove host cell proteins from the product monoclonal antibody. Host cell proteins have a wide range of molecular weights and charge, but more than 99% of these proteins are smaller than the size of the monoclonal antibody.

In other embodiments, HPCMP can be used for purification of conjugated proteins and polysaccharides. This includes the removal of unreacted protein and polyethylene glycol (PEG) in the purification of pegylated proteins as well as the removal of unreacted protein and polysaccharides in the purification of glycoconjugate vaccines. HPCMP can also be used to remove unreacted drug molecules in the purification of antibody-drug conjugates.

Methods and systems for designing and using membranes with appropriate pore size for targeting product separations of interest for use in HPCMP systems are also provided. HPCMP optimization can include the selection of buffer conditions (e.g., ionic strength and pH of the buffer as it relates to the isoelectric point of the product and impurity proteins). This can allow for enhancement of the transmission of the impurity across the membrane while increasing the retention of the desired product.

Desired operating conditions (e.g., flow rates as well as pH and ionic strength) for the HPCMP process can be selected to achieve a target purification factor and target yield. The target yield can be over 90%, over 95% or over 98% in some embodiments. In some embodiments, a chemical pretreatment can be used to adjust the pore size of the membrane(s) prior to operation of the HPCMP process. For example, a pretreatment can be provided to pretreat at least one membrane of the HPCMP module so that the HPCMP module can purify larger biomolecules.

In some embodiments, ultrafiltration (UF) and buffer exchange (e.g. countercurrent dialysis (CCD)) steps can be utilized before the HPCMP process to adjust the product concentration and buffer. Further reductions in operating costs may be achieved by running the dialysate buffer through subsequent unit operations. For example, the Clarified Cell Culture Fluid (CCF) from the bioreactor can be processed by UF→CCD→HPCMP→polishing, while the dialysate/draw solution (which can also be referred to as the buffer) can run in a countercurrent arrangement going from a CCD process and/or UF before it is passed to the HPCMP and subsequently output in a waste flow. For such embodiments, the dialysate solution (or the buffer flow) can first be used for the final buffer exchange and then as the draw solution to remove host cell proteins from within the feed fed to the HPCMP module. This would not only significantly reduce buffer consumption, it could also reduce the number of pumps needed for the combined unit operations (e.g. using multiple pump-heads on each pump). In this case, the UF retentate, CCD feed and retentate, and HPCMP feed and retentate would all be operating at the same flow rate (e.g. driven by a first pump) while all the dialysate and draw streams could be potentially operated at the same flow rates (e.g. driven via a second pump).

Other applications for embodiments of the HPCMP system and method can include natural protein product separations including dairy products (e.g., whey proteins), egg proteins, and plasma proteins. Such embodiments can be utilized in conjunction with dairy processing, food production, or other types of animal protein processing. These complex feeds contain multiple valuable protein products, with the HPCMP system and method utilized to increase the purity of one or more of these proteins in the product output flow and one or more of these proteins in the output draw solution flow.

A method of separating proteins is provided that can include: passing a feed to a High Performance Countercurrent Membrane Purification (HPCMP) module having at least one membrane within a vessel where the feed comprises a first protein and a second protein. The feed can be passed through the HPCMP module in countercurrent flow with a buffer fed to the vessel of the HPCMP module. The method can also include outputting a product flow and a buffer draw solution outlet flow from the vessel of the HPCMP module. The product flow can have a purity of the first protein that is greater than the purity of the first protein within the feed and the buffer outlet flow can have a purity of the second protein that is greater than the purity of the second protein within the feed passed to the HPCMP module. The method can be performed so that the passing of the feed and the outputting of the product flow and the buffer outlet flow occur simultaneously during a continuous flow operation of the HPCMP module. The method can also be performed so that the passing of the buffer flow, passing of the feed, outputting of the product flow and buffer outlet flow occur simultaneously during a continuous flow operation of the HPCMP module.

In some embodiments, at least one membrane of the module can be a single use membrane. In other embodiments, the membrane can be a multiple use membrane. In some embodiments, the at least one membrane can be a hollow fiber membrane. In other embodiments, the membrane can have another type of configuration.

The method can be performed in some embodiments so that the purity of the first protein within the product flow is at least fifty times higher than the purity of the first protein within the feed. The purity of the second protein within the buffer outlet flow can be at least fifty times higher than the purity of the second protein within the feed as well. In some embodiments, the purity of the first protein within the product flow is at least 100 times higher than the purity of the first protein within the feed and the purity of the second protein within the buffer outlet flow is at least 100 times higher than the purity of the second protein within the feed. In other embodiments, the purities may have other values to meet a particular set of design criteria or separation objectives (e.g. between 50 times higher and 100 times higher, between double to 100 times higher, etc.).

The feed, buffer, product flow, and buffer outlet flow can each be flows of fluid or streams of fluid. For example, in some embodiments the feed can be a liquid flow and the buffer can be a liquid flow as well. The product flow can be a liquid flow and the buffer outlet flow can also be a liquid flow.

Embodiments of the method can include other steps. For instance, the method can include outputting the feed from a bioreactor upstream of the HPCMP module and passing the feed through at least one of ultrafiltration (UF) and dialysis upstream of the HPCMP module (e.g. passing the feed through UF and/or dialysis upstream of the HPCMP module). Additional downstream processing of the product flow or buffer outlet flow can also be performed (e.g. polishing, additional separations, etc.). In some embodiments, the dialysis can be countercurrent dialysis (CCD) or another type of dialysis. In some embodiments, the method can include passing the buffer through at least one of ultrafiltration (UF) and dialysis before the buffer is fed to the HPCMP module (e.g. passing the buffer through UF and/or dialysis before the buffer is fed to the HPCMP module). The dialysis of the buffer can be a countercurrent dialysis (CCD) in some embodiments.

As another example, the method can also include controlling at least one of ionic strength of the feed and pH of the feed to increase selectivity. The method can also (or alternatively) include other steps, such as adjusting at least one of ionic strength of the buffer and pH of the buffer during the continuous operation of the HPCMP module to increase selectivity.

As yet another example, the method can include pretreating the at least one membrane to increase an effective pore size of the at least one membrane. This pretreating can occur prior to the feed being passed through the HPCMP module.

The first protein can be within a mixture of first and second proteins or be in a mixture of a single first protein and a single second protein, or in a mixture of a first protein and multiple second proteins, or in a mixture that includes the first protein, a second protein, and at least one third protein. In some embodiments, the first protein can be a monoclonal antibody, bovine serum albumin (BSA), myoglobin (Mb), or Immunoglobulin G (IgG) and the second protein is a protein within a mixture of host cell proteins, BSA, Mb, or IgG. The second protein can be different from the first protein so if the first protein is BSA, the second protein would be a different protein, for example.

A separation apparatus is also provided. The separation apparatus can be configured to perform an embodiment of the separation method. In some embodiments, the separation apparatus can include a High Performance Countercurrent Membrane Purification (HPCMP) module having at least one membrane within a vessel. The HPCMP module can be configured to receive a feed comprising a first protein and a second protein so that the feed is passable through the HPCMP module in countercurrent flow with a buffer fed to the vessel of the HPCMP module. The HPCMP module can be configured to output a product flow and a buffer outlet flow from the vessel of the HPCMP module so that the product flow has a purity of the first protein that is greater than the purity of the first protein within the feed and the buffer outlet flow has a purity of the second protein that is greater than the purity of the second protein within the feed to the vessel of the HPCMP module. The HPCMP module can be configured so that the feed is received into the vessel simultaneously the product flow and the buffer outlet flow being output from the vessel during continuous flow operation of the HPCMP module. In other embodiments, the HPCMP module can be configured so that the feed is received into the vessel simultaneously with the buffer fed into the module and also simultaneously with the product flow and the buffer outlet flow being output from the vessel during continuous flow operation of the HPCMP module.

Embodiments of the separation apparatus can also include a bioreactor upstream of the HPCMP module to generate the feed to pass through the HPCMP module. There can also be at least one of an ultrafiltration (UF) unit and a dialysis unit positioned upstream of the HPCMP module to process the feed through at least one of ultrafiltration (UF) and dialysis upstream of the HPCMP module before the feed is fed to the HPCMP module. Embodiments can also include at least one of an ultrafiltration (UF) unit and a dialysis unit positioned upstream of the HPCMP module to process the buffer through at least one of ultrafiltration (UF) and dialysis upstream of the HPCMP module before the buffer is fed to the HPCMP module.

The separation apparatus can also include a plurality of sensors positioned to monitor the HPCMP module, the product flow and the buffer outlet flow and a controller connected to the sensors.

The at least one membrane of the HPCMP module can be a hollow fiber membrane and/or a single use membrane in some embodiments. In other embodiments, the membrane may have a different configuration or be a multiple use membrane.

A method of separating biological material is also provided. Embodiments of the method can include passing a feed to a High Performance Countercurrent Membrane Purification (HPCMP) module having at least one membrane within a vessel, the feed comprising a first desired biological product and at least one second component, the feed passed through the HPCMP module in countercurrent flow with a buffer fed to the vessel of the HPCMP module. The method can also include outputting a product flow and a buffer outlet flow from the vessel of the HPCMP module. The product flow can have a purity of the first desired biological product that is greater than the purity of the first desired biological product within the feed and the buffer outlet flow can have a purity of at least one second component that is greater than the purity of the second component within the feed passed to the HPCMP module. The passing of the feed and the outputting of the product flow and the buffer outlet flow can occur simultaneously during a continuous flow operation of the HPCMP module. The passing of the feed and the buffer as well as the outputting of the product flow and the buffer outlet flow can occur simultaneously during a continuous flow operation of the HPCMP module in some embodiments.

Embodiments of the method can be employed so that the purity of the first desired biological product within the product flow can be at least fifty times higher than the purity of the first desired biological product within the feed or can be at least 100 times higher than the purity of the first desired biological product within the feed. The purity of the at least one second component within the buffer outlet flow can at least fifty times higher than the purity of at least one second component (e.g. a second impurity or a second protein, etc.)

within the feed or can be at least 100 times higher than the purity of the at least one second component (e.g. a second impurity or a second protein, etc.) within the feed.

In some embodiments, the first desired biological product can be a pegylated protein, glycoconjugate vaccine, or antibody drug conjugate and the second component can be a second impurity, unreacted polyethylene glycol, polysaccharide, or a drug molecule. In other embodiments, the first desired biological product can be a first protein, a mixture of first proteins, a monoclonal antibody, bovine serum albumin (BSA), myoglobin (Mb), or Immunoglobulin G (IgG) and the second component can be a second protein, a mixture of second proteins, a second impurity, a mixture of second impurities, a protein within a mixture of host cell proteins, BSA, Mb, or IgG.

A separation apparatus can be provided to employ a method of separating biological material. Embodiments of the apparatus can include a High Performance Countercurrent Membrane Purification (HPCMP) module having at least one membrane within a vessel. The HPCMP module can be configured to receive a feed comprising a first desired biological product and a second component so that the feed is passable through the HPCMP module in countercurrent flow with a buffer fed to the vessel of the HPCMP module. The HPCMP module can be configured to output a product flow and a buffer outlet flow from the vessel of the HPCMP module so that the product flow has a purity of the first desired biological product that is greater than the purity of the first desired biological product within the feed and the buffer outlet flow has a purity of the second component that is greater than the purity of the second component within the feed to the vessel of the HPCMP module. The HPCMP module can be configured so that the feed is received into the vessel simultaneously with the product flow and the buffer outlet flow being output from the vessel during continuous flow operation of the HPCMP module. Embodiments can be configured so that the HPCMP module can be configured so that the feed is received into the vessel simultaneously with buffer fed to the vessel as well as the product flow and the buffer outlet flow being output from the vessel during continuous flow operation of the HPCMP module.

Embodiments of the separation apparatus can be configured so that the purity of the first desired biological product within the product flow is at least fifty times higher than the purity of the first desired biological product within the feed. The purity of the at least one second component within the buffer outlet flow can be at least fifty times higher than the purity of at least one second component within the feed.

Embodiments of the separation apparatus can also be configured so that the purity of the first desired biological product within the product flow is at least 100 times higher than the purity of the first desired biological product within the feed and the purity of at least one second component within the buffer outlet flow is at least 100 times higher than the purity of at least one second component within the feed.

In some embodiments, the first desired biological product can be a pegylated protein, glycoconjugate vaccine, a first protein or an antibody drug conjugate and the second component can be a second impurity, a second protein, the unreacted polyethylene glycol, polysaccharide, or drug molecule.

In some embodiments of the separation apparatus, the first desired biological product is a monoclonal antibody, a first protein, a mixture of first proteins, bovine serum albumin (BSA), myoglobin (Mb), or Immunoglobulin G (IgG) and the second component is a protein within a mixture of host cell proteins, a second protein, a mixture of second proteins, BSA, Mb, or IgG. In such embodiments, if the first protein is BSA, the second protein may not include BSA.

In embodiments of the apparatuses and methods, the buffer flow can be considered a buffer draw solution flow and the buffer outlet flow can be a buffer draw solution outlet flow. The product flow can be considered a first product flow and the buffer outlet flow, or buffer draw solution outlet flow, can be considered a second product flow.

It should be appreciated that embodiments of the methods and apparatuses can be utilized to provide separations for mixtures of many proteins or other biological materials or a separation of a mixture that includes only a first protein mixed with a second protein within a solution that may include other materials (e.g. water, host cellular material, electrolytes, etc.). Embodiments can be employed in dairy protein separation, animal protein separation, biological material separation, or other types of protein separation applications or biological material separations. Some embodiments of the apparatus can be included in a plant, can be retrofit into a pre-existing plant, or can be a standalone separation processing plant.

Other details, objects, and advantages of the invention will become apparent as the following description of certain exemplary embodiments thereof and certain exemplary methods of practicing the same proceeds.

BRIEF DESCRIPTION OF THE DRAWINGS

Exemplary embodiments of a high performance counter-current membrane purification (HPCMP) system are shown in the accompanying drawings and certain exemplary methods of making and practicing the same are also illustrated therein. It should be appreciated that like reference numbers used in the drawings may identify like components.

DETAILED DESCRIPTION

Figure 1:
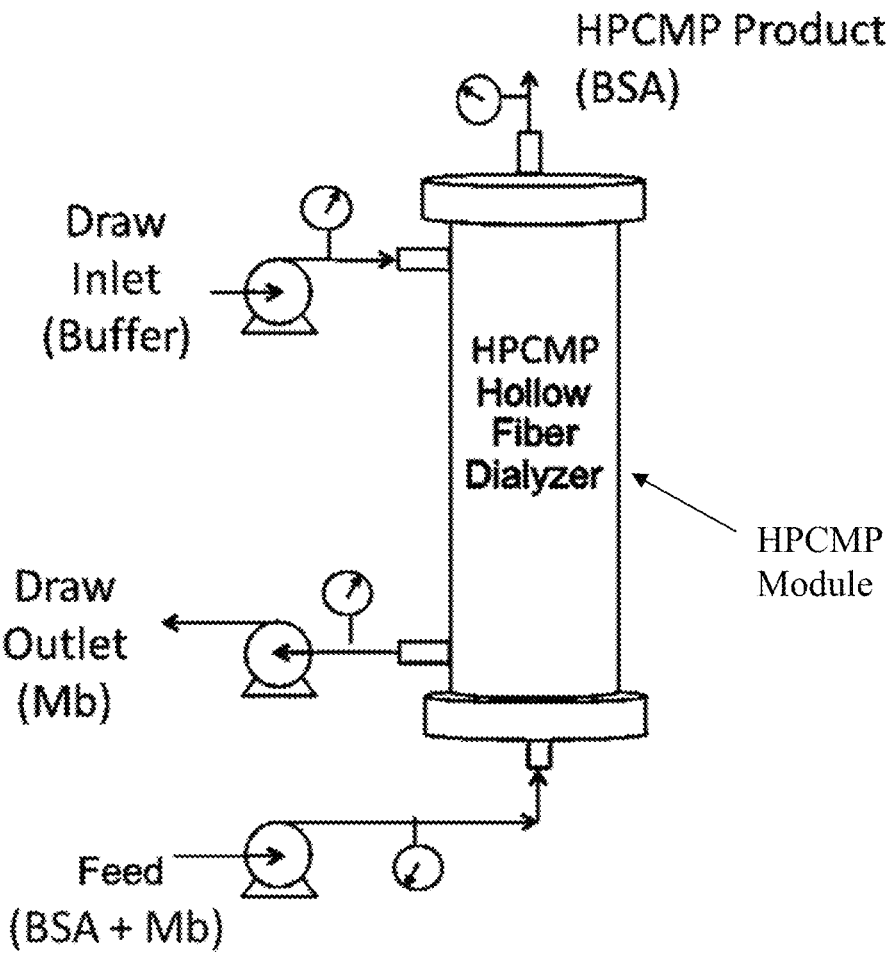
FIG. 1 is a schematic view of a first embodiment of a HPCMP system.

Referring to FIGS. 1, 15, and 19-20 embodiments of a separation apparatus configured for high performance countercurrent membrane purification (HPCMP) can include a feed that includes at least two proteins (e.g. at least one monoclonal antibody mixed with a mixture of proteins, at least one monoclonal antibody mixed with a mixture that includes at least one second protein, a feed that includes bovine serum albumin (BSA) and myoglobin (Mb), BSA and Immunoglobulin G (IgG), a combination of two other proteins, a combination of BSA and Mb along with at least one other protein and/or other material, a combination of BSA and IgG along with at least one other protein and/or other material, etc.) fed to at least one HPCMP module of the HPCMP system. It should be appreciated that the feed including the two or more proteins can also include other components (e.g. water, cell material, etc.). The feed can be a feed flow received from a bioreactor, for example. The feed can be a fluid. For example, the feed can be a liquid feed that includes at least one product and one impurity as well as other components and impurities (e.g. water, cellular material, electrolytes, etc.). For example, the product can be a pegylated protein, a conjugated polysaccharide, or an antibody-drug conjugate, with the impurity being the unreacted components (e.g., PEG, polysaccharide, protein, or drug molecules). In some embodiments, a first pump can be provided that is in fluid connection with the feed conduit and vessel of the HPCMP module to help drive the flow of feed to the HPCMP module.

The feed can include a concentration of a first protein or first desired product within a range of 0.1 g/L to 300 g/L, 1 g/L to 40 g/L, or other suitable concentration. The feed can include a concentration of the second protein or a second component that is higher than, equal to, or lower than the concentration of the first protein or first desired product. The feed can also include other components, such as, for example, water, cellular material, and electrolytes, etc.

Buffer, which can also be referred to as the draw solution, is fed to the HPCMP module so that the buffer flows through the module in a flow direction that is countercurrent to the flow direction at which the feed is passed through the module. For example, the feed can be passed in a first vertical flow direction (e.g. upwardly or downwardly) through the module and the buffer can be passed in a second vertical flow direction that is opposite the first vertical flow direction through the module (e.g. downwardly when the first vertical flow direction is upwardly or upwardly when the first vertical flow direction is downwardly). As another example, the feed can be passed in a first lateral flow direction (e.g. leftwardly or righwardly) and the buffer can be passed in a second lateral flow direction that is opposite the first lateral flow direction (e.g. leftwardly when the first lateral flow direction is rightwardly or rightwardly when the first lateral flow direction is leftwardly).

The buffer flow rate fed to the HPCMP module can be fed at a higher flow rate than the feed (e.g. feed from a bioreactor) is fed into the HPCMP for separation of the feed. For example, in some embodiments, the buffer feed flow rate into the HPCMP module can be from one to ten times that of the feed flow rate. For an embodiment of the HPCMP module having a 2 square meter membrane area, this can correspond to 1 mL/min to 200 mL/min in some embodiments.

The buffer passed through the HPCMP module can be a fluid. At least one second pump can be provided in fluid communication with a buffer conduit and the vessel of the HPCMP module to help drive the flow of buffer to the HPCMP module in a countercurrent direction relative to the feed flow driven by the first pump. The buffer fed to the HPCMP module may not include any protein (e.g. does not have any protein, does not include the first protein, does not include the first product within the feed, does not include the second protein, does not include a particular impurity or a particular set of impurities within the feed that is to be separated out of the feed, etc.). The buffer can include other components, such as, for example, water and electrolytes, etc. that can provide the buffer with a pre-selected ionic strength and a pre-selected pH level to facilitate separation of the second protein from the first protein within the HPCMP module via the at least one membrane positioned therein when the buffer is passed through the module in countercurrent flow arrangement with the feed.

The feed can also undergo upstream processing before the feed is fed to the HPCMP module. For example, the feed can undergo ultrafiltration (UF) or countercurrent dialysis (CCD) before being fed to the HPCMP module to undergo HPCMP separation (see e.g. FIG. 19).

The feed, which can include a mixture of proteins that includes the desired first product or first protein and the second protein or second impurity as well as other material, can be fed into a HPCMP hollow fiber module that includes at least one hollow fiber membrane within a vessel to undergo HPCMP separation. The HPCMP hollow fiber module can also receive a buffer feed that is passed into the shell side of the vessel of the module having one or more hollow fiber membranes therein so that the buffer is passed from the shell inlet to the shell outlet. The feed can pass through the lumen inlet of the vessel of the module in a first feed flow direction that is countercurrent to the direction at which the buffer flows along the shell side of one or more hollow fiber membranes within the vessel of the HPCMP hollow fiber module for undergoing separation so that a majority of a first protein or other first desired product within the mixture (e.g. BSA, IgG) can be output from the lumen outlet of the module in the retained solution, while a substantial portion of at least one second protein or second impurity within the mixture of the feed (e.g. Mb, BSA, etc.) can be separated from the first protein or first product and output with the buffer via the buffer shell outlet (which can also be called the draw solution output). The output flow having a substantial portion of the first protein or first desired product output from the HPCMP module can include over 70%, over 80%, over 90%, over 95%, up to 99%, or from 95%-100% of the first protein or first desired product within the feed as well as no more than 30%, no more than 20%, no more than 10%, no more than 5%, or no more than 1% of the second protein or second impurity from within the feed.

In some embodiments utilizing a module having 2 square meters of membrane area, the concentration of the first protein or first desired product within the output flow can be, for example, between 1 g/L and 40 g/L of the first protein or first product and the output flow can be output at a flow rate of between 1 mL/min and 20 mL/min. Other embodiments utilizing different modules having different sized membranes can utilize other concentrations and other flow rates as may be suitable to meet a particular set of design and operational criteria.

In some embodiments, the recovery of the first protein or first desired product within the output product flow including a majority of the first protein or first desired product can include up to 90% of the first protein or first desired product (e.g. 70%-90%, 80%-90%), between 60-99.9% of the first protein or first desired product, up to 100% and not less than 95%, or other recovery of the first protein or first desired product from within the feed fed to the HPCMP module. The second protein or second impurity can be present in a concentration of up to 50% of the feed concentration, (e.g. 0-50%), less than 10% of the feed concentration or above 0% and below 5% of the second protein or second impurity in the feed fed to the HPCMP module to undergo separation from the first protein or first desired product. Other elements can also be included in the product output flow (e.g. a third protein, electrolytes, cellular matter, etc.).

The buffer outlet flow can be a waste flow or can be a second product flow that includes the second protein (e.g. Mb, BSA, etc.). For example, in some embodiments, a product can be collected in the draw solution flow output from the HPCMP module. For example, the buffer outlet flow can include a significant amount of the second protein from the feed as well as a minor amount of the first protein or first desired product from within the feed. In some embodiments, the buffer outlet flow can include over 70%, (e.g. 70% to 100%), over 80%, over 90%, over 95%, up to 99%, or from 95%-100% of the second protein within the feed as well as no more than 30%, no more than 20%, no more than 10%, no more than 5%, or no more than 1% of the first protein or first desired product from within the feed. In some embodiments, the concentration of the second protein within the buffer outlet flow including a majority of the second protein can include up to 90 percent (90% by mass) of the second protein, between 60-99.9 mass % of the second protein, or other percentage of the second protein. The first protein or first desired product can be present in a concentration of up to 10% by mass, 1%-40% by mass, or less than 1% by mass of the first protein within the feed flow. Other elements can also be included in the buffer outlet flow (e.g. a third protein, PEG, electrolytes, cellular matter, etc.). In some embodiments, the buffer outlet flow can contain the product from the HPCMP module, with the second protein collected in the retentate outlet flow.

Figure 19:
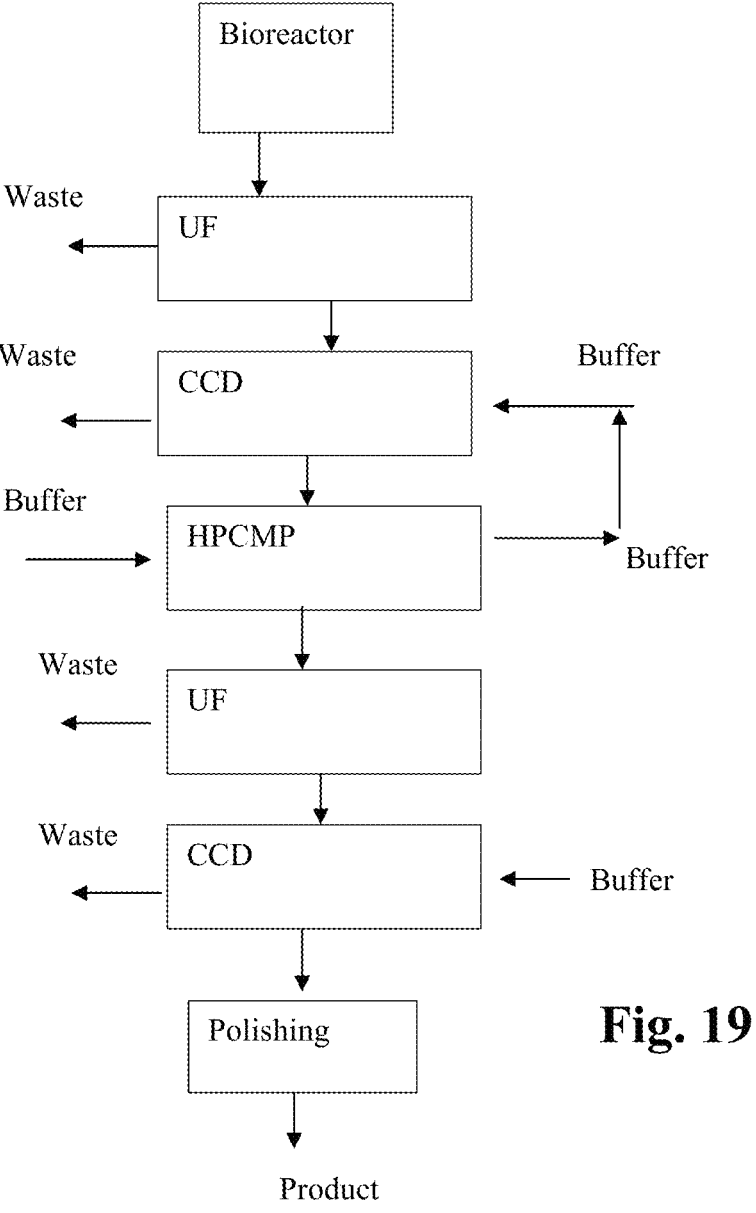
FIG. 19 is a schematic view of another exemplary embodiment of a HPCMP system.

The output product flow including a substantial portion of the first protein or first desired product that is output from the HPCMP hollow fiber module can undergo other downstream processing, as may be appreciated from FIG. 19. For example, the output flow comprising a substantial amount of the first protein or first desired product as well as a significantly reduced amount of the second protein or second impurity can undergo ultrafiltration (UF), countercurrent dialysis (CCD), and polishing before being output as a purified product from the system. The buffer outlet flow that includes a substantial portion of the second protein or second impurity and a minor portion of the first protein or first desired product from the feed (e.g. 80% or more than 80% of the second protein within the feed and 20% or less than 20% of the first protein within the feed) can also undergo other processing (e.g. CCD, UF, etc.) so that another product flow that includes the second protein can be provided or so that the buffer outlet flow can be used in other process units (e.g. a CCD unit downstream of the HPCMP module, another unit upstream of the HPCMP module, another process unit of another system within a plant, etc.) before being output as waste.

The buffer outlet flow can be comprised of the second protein that is to be separated from the first protein or first desired product in the HPCMP module. In some embodiments, there can be a second pump in fluid communication with the buffer outlet flow conduit to help drive the flow of buffer through the buffer outlet flow conduit to another unit or vessel of the system or other unit of a plant that can include the HPCMP module or HPCMP system.

The buffer that is passed through the HPCMP system can also include other components (e.g. water, electrolytes, etc.). The feed and/or buffer fed into the HPCMP module can be composed to help provide a pre-selected condition within the HPCMP module to facilitate desired separation of the first protein or first desired product from the second protein or second impurity (e.g. help provide a desired pH level within the HPCMP module, help provide an ionic strength within a pre-selected range, help drive a desired selectivity of the membrane(s) within the module to facilitate at least a pre-selected target amount of separation of the first protein or first desired product from the second protein or second impurity, etc.). In some embodiments, the buffer flow fed to the HPCMP module can be considered a draw solution or dialysate flow (e.g. the buffer flow can be a dialysate flow). The buffer flow output from the HPCMP module can include the components included in the buffer fed to the HPCMP module and can also include a significant increase in the second protein within that flow as well as an increase in first protein or first desired product within the buffer that is output from the HPCMP module as a result of the countercurrent separation that occurs in the HPCMP module via the at least one membrane positioned therein.

As may best be appreciated from FIG. 19, in some embodiments the feed flow output from a bioreactor can be processed via ultrafiltration (UF) and buffer exchange (e.g. countercurrent dialysis (CCD)) before the HPCMP module (e.g. upstream of the HPCMP module) to adjust the antibody concentration and buffer properties. Further reductions in operating costs can also be achieved by running the buffer through subsequent unit operations. For example, the feed output from the bioreactor can be processed by UF→CCD→HPCMP→polishing, while the buffer (e.g. dialysate/draw solution etc.) can run in a countercurrent arrangement going from CCD→HPCMP→waste or second product flow. For such embodiments, the buffer can first be used for the final buffer exchange and then to remove host cell proteins. This would not only significantly reduce buffer consumption, it can also reduce the number of pumps needed for the combined unit operations (e.g. using multiple pump-heads on each pump). In this case, the UF retentate, CCD feed and retentate, and HPCMP feed and retentate can all be operating at the same flow rate (e.g. driven by a first pump) while all the buffer streams (e.g. dialysate and draw streams) can be operated at the same flow rates (e.g. driven via a second pump).

In some embodiments, the system can be configured so that the HPCMP module undergoes a pretreatment so that at least one membrane of the HPCMP module is pretreated so that the HPCMP can purify larger biomolecules. The pretreatment can occur before the HPCMP module is utilized in a continuous operational process for separation of at least one first protein or first desired product from a feed, which can be an output flow from a bioreactor, for example.

Figure 20:
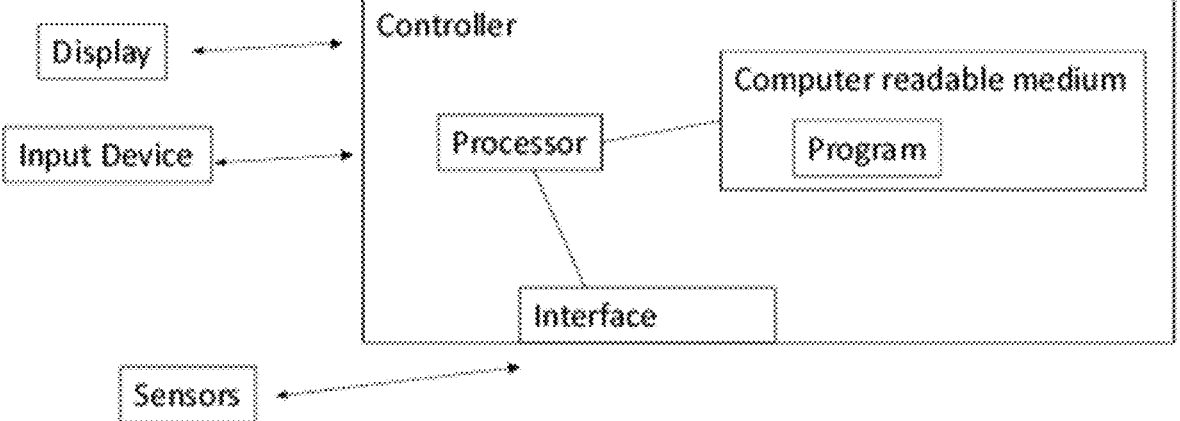
FIG. 20 is a block diagram of an exemplary controller that can be utilized in the HPCMP system embodiments shown in FIGS. 1, 15, and 19.

It should be appreciated that embodiments of the system utilizing the HPCMP module can include conduits for connection of the buffer, feed, waste, and output flows between different units as well as appropriate valves and sensors. In some embodiments, an automated process control system can be run on a workstation to control operation of the system. An example of a controller that can provide automated control for embodiments of the HPCMP system or apparatus utilizing the HPCMP system that can be provided to receive data from these sensors and adjust operations of different elements based on the received sensor data is shown in FIG. 20. The controller can include a processor connected to a non-transitory computer readable medium and at least one interface for communications with the sensors. The processor can run at least one automated control program stored in the computer readable medium (e.g. non-transitory memory, flash memory, etc.) that defines a method for controlling the operation of the plant and/or one or more elements of the plant (e.g. the HPCMP system). For example, the controller can be configured to adjust operations of one or more pumps or other elements to adjust concentrations of the first protein or first desired product within a first product flow and/or adjust the concentration of the second protein or second impurity within the waste flow(s) or second product flow. An operator can provide input to the controller for adjusting operational setpoints or other targets via an input device (e.g. mouse, keyboard, pointer device, touch screen, etc.) communicatively connected to the controller and the controller can generate one or more graphical user interfaces on a display communicatively connected to the controller to facilitate receipt of input from an operator and also provide output (e.g. sensor data, warnings, etc.) to the operator.

As can be appreciated from FIGS. 1, 15, and 19-20, a method of separating a first protein or first desired product from a second protein or second impurity can include passing a feed to a HPCMP module having at least one membrane within a vessel where the feed includes a first protein or first desired product and a second protein or second impurity. The feed can be passed through the HPCMP module in countercurrent flow with a buffer fed to the vessel of the HPCMP module. The HPCMP module can be operated to output a product flow and a buffer outlet flow from the vessel of the HPCMP module. The product flow can have a purity of the first protein or first desired product that is greater than the purity of the first protein or first desired product within the feed. The HPCMP module can be operated so that the passing of the feed and the outputting of the product flow and the buffer outlet flow occur simultaneously during a continuous flow operation of the HPCMP module. One or more of the membranes (e.g. all the membranes or each membrane of the HPCMP module) can be a single use membrane and/or a hollow fiber membrane.

The HPCMP module can be operated to provide high performance separation. For example, the purity of the first protein or first desired product within the product flow can be at least fifty times higher than the purity of the first protein or first desired product within the feed or at least 100 times higher than the purity of the first protein or first desired product within the feed. As another example, the purity of the second protein within the buffer outlet flow can be at least fifty times higher than the purity of the second protein within the feed or at least 100 times higher than the purity of the second protein within the feed.

In some embodiments, the separation process may purify multiple first products (e.g., first protein, mixture of first proteins, etc.) within a feed while also separating multiple second impurities (e.g second protein, mixture of second proteins, etc.) from the output low output from the HPCMP module. For example, there may be a mixture of proteins within the feed that include multiple first proteins and multiple second proteins. Separation can be performed via the HPCMP module and flow of buffer to separate the second proteins from the first protein so a first product flow has a higher purity of first proteins. The draw output from the HPCMP module can have an increased purity of the mixture of second proteins separated from the feed as well. It should therefore be appreciated that separation of a first protein from a second protein can also include situations in which a feed can undergo separation via at least one HPCMP module so that mixtures of first proteins are separated from mixtures of second proteins.

In some embodiments, the buffer can be adjusted or controlled so that at least one of ionic strength of the buffer and pH of the buffer is adjustable to improve the separation performance of the HPCMP module. This can be performed during continuous operation of the HPCMP module.

The HPCMP module can also undergo pretreatment. For example, at least one membrane can be pretreated so that the HPCMP module can purify larger biomolecules.

A bioreactor can be positioned upstream of the HPCMP module to generate the feed to pass through the HPCMP module. At least one ultrafiltration (UF) unit and dialysis unit can be positioned upstream of the HPCMP module to process the feed through at least one ultrafiltration (UF) and dialysis process, upstream of the HPCMP module before the feed is fed to the HPCMP module. At least one of an ultrafiltration (UF) unit and a dialysis unit can also be positioned to process the buffer through at least one of ultrafiltration (UF) and dialysis before the buffer is fed to the HPCMP module.

A plurality of sensors can be positioned to monitor the HPCMP module, the product flow and the buffer outlet flow as well as the feed and buffer flows. A controller can be communicatively connected to the sensors to receive sensor data from the sensors to facilitate automated control of the HPCMP module or HPCMP system.

Experimentation was conducted to evaluate the potential performance embodiments that the HPCMP system could provide for separation of proteins. A discussion of these experiments and the results obtained are shown below.

First Set of Experimental Studies—Evaluation of Separation Results

A first set of experiments was performed with BSA (molecular weight (MW)=66 kilodaltons (kDa)) and myoglobin, Mb (MW=17 kDa) as an exemplary set of first and second proteins to be mixed within a feed for subsequent separation. Both of these protein materials used in the first set of experiments were obtained from Sigma-Aldrich (Catalog numbers A2153 and MO630, respectively). Feed solutions were prepared by dissolving the BSA and Mb in 1× phosphate buffered saline (PBS) buffer made by diluting a 10× concentrate (Thermo Scientific, Waltham, MA) with DI water to yield a final solution with conductivity of approximately 15 mS/cm and pH 7.8. Sodium azide was added at 0.02% w/v to prevent microbial growth during long experimental runs. All solutions were pre-filtered through 0.2 µm polyvinylidene fluoride (PVDF) membranes prior to use to remove undissolved protein aggregates.

Protein separations were performed using Purema™ H hollow fiber dialyzers from 3M Company (St. Paul, MN) containing 13,200 fibers made from a blend of polyethersulfone (PES) and polyvinylpyrrolidone (PVP). The fibers had an inner diameter of 200 µm, wall thickness of approximately 30 µm, and active length of 23.3 cm, giving a surface area of 1.9 m². Modules were operated in a vertical orientation with the draw solution introduced into the top port on the shell side of the module as shown schematically in the exemplary embodiment of the HPCMP module illustrated in FIG. 1.

The protein feed was introduced into the lumen-side inlet at the bottom of the module, i.e., in countercurrent flow to the draw solution. Flow rates were controlled with Masterflex L/S peristaltic pumps (Cole-Parmer, Vernon Hills, IL) fitted with Tygon® E-LFL tubing (Cole-Parmer). A single pump equipped with two pump heads was used to control the inlet and outlet flowrates of the draw solution and thus maintain close to zero net ultrafiltration. Pumps were calibrated before each experiment, with the flow rates evaluated during the experiment by timed collection. Pressure gauges (Ashcroft, Stratford, CT) were placed immediately before/after the inlet and outlet ports. Before each experiment, the module was completely flushed with PBS buffer. The feed was then replaced with the protein mixture with samples collected periodically from the feed, draw exit, and retentate exit lines for evaluation of the concentrations of the BSA and Mb concentrations.

BSA and Mb concentrations were evaluated by UV absorbance at 280 and 408 nm using an Infinite® m200 Pro microplate reader (Tecan Trading AG, Switzerland). Calibration curves were constructed for each protein by measuring the absorbance at both wavelengths for a series of samples at known concentrations. More detailed analysis of the protein mixtures was performed using an Agilent 1260 infinity II HPLC system (Agilent Scientific instruments, Santa Clara, CA) with Ultrahydrogel 2000, 500 and 120 size exclusion columns in series (Waters Corp, Milford, MA); a guard column was placed immediately before the Ultrahydrogel 2000 column. The HPLC was operated at a constant running buffer (PBS) flow rate of 0.6 mL/min, with the column temperature maintained at 30° C. Samples were injected every 60 min and detected by a refractive index detector.

Limited experiments were also performed using polydisperse dextrans using both HPCMP and pressure-driven (ultrafiltration) modes. Ultrafiltration was performed without any countercurrent flow solution in the shell side of the module, with the permeate exit pump used to control the ultrafiltration rate. The dextran feed was prepared by mixing dextrans of various MWs including 0.2 g/L of Dextran T10 (9-11 kDa), 0.2 g/L of Dextran T40 (35-45 kDa), 0.8 g/L of Dextran T150 (150 kDa), and 1.8 g/L of Dextran T2000 (2000 kDa), obtained from Sigma-Aldrich (St. Louis, MO) and TCI Chemical (Portland, OR). Column calibration was performed using EasiVial polyethylene oxide (PEO) standards (Agilent Scientific instruments).

The transport properties of the hollow fiber membranes were first examined using polydisperse dextrans. Experiments were performed using both filtration and HPCMP modes of operation.

For the filtration experiments of the first set of experiments, the data are plotted as the fractional transmission through the membrane, which is equal to the membrane sieving coefficient:

$$S = \frac{C_{permeate}}{C_{feed}} \tag{1}$$

with the system operated using $g_{feed}$=500 mL/min and $q_p$=200 mL/min.

The HPCMP experiments were performed using phosphate buffer as the draw solution using $g_{feed}$=0.5 ml/min and $q_d$=6.1 ml/min, with the fractional dextran removal evaluated as:

$$F = 1 - \frac{C_{retentate}}{C_{feed}} \tag{2}$$

In both cases, the concentrations of the different molecular weight dextrans were evaluated by HPLC based on the area under narrow slices of the chromatogram. Data were obtained after the solute concentrations in the permeate and retentate solutions had stabilized; this required about 15 min for the sieving (pressure-driven filtration) and 8 hr for the HPCMP. The much longer time required for the HPCMP experiments is due to the slower rate of dextran diffusion.

Figure 2:
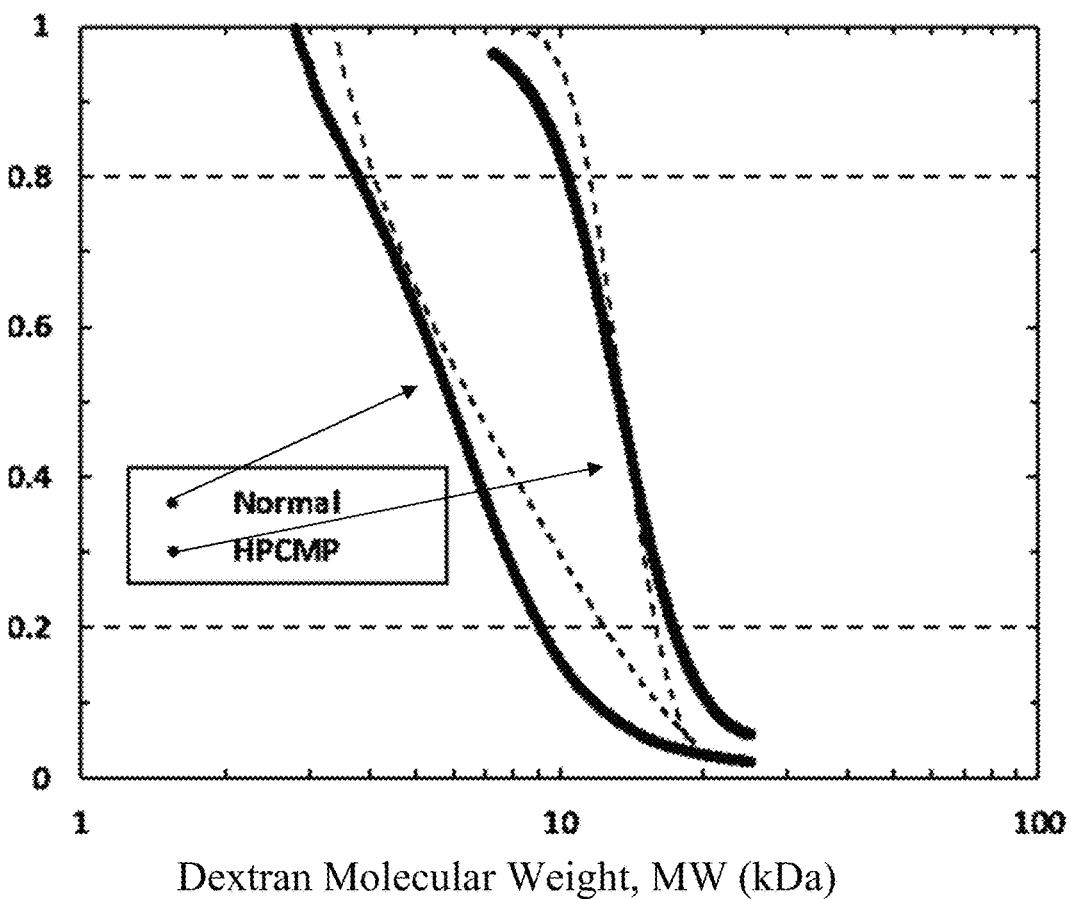
FIG. 2 is a graph illustrating a comparison of normal processing conditions and use of HPCMP processing conditions. The y-axis provides values for the sieving coefficient, $S_o$ and also the fractional removal $R_f$ for the normal (left most set of lines) and HPCMP (right most set of lines) operational conditions. Modeled results are shown as dashed lines and the solid lines illustrate the observed values from experimentation using a particular embodiment.

As shown in FIG. 2, the dextran sieving coefficients and fractional removal rates were both equal to 100% for the very small dextrans which are easily transported across the membrane but decrease to zero for very large dextrans that are fully retained by the membrane pores. The HPCMP results are shifted to the right and appear much steeper than the sieving curve, indicating that diffusive transport has the potential to provide for a more selective separation than is possible using pressure-driven filtration. For example, if we look at conditions that provide sieving coefficients and fractional removal rates of 80 and 20%, the sieving curve yields a MW ratio for the corresponding dextrans of 2.5 while the HPCMP results yield a MW ratio of only 1.5.

Table 1, below, provides a summary of HPCMP results from some of the first set of experiments.

TABLE 1

Summary of HPCMP results for BSA-Mb separation Experiments

| Experiment | $C_{BSA}$ (g/L) | $C_{Mb}$ (g/L) | $q_F$ (mL/ min) | $q_D$ (mL/ min) | A | $Y_{Mb}$ | $P_{Mb}$ |
|---|---|---|---|---|---|---|---|
| 1 | 40 | 0.5 | 2.0 | 8.0 | 4.0 | 82% | >600 |
| 2 | 2 | 0.45 | 0.5 | 6.1 | 12 | 98% | >300 |
| 3 | 2 | 0.5 | 0.5 | 6.4 | 13 | 99.5% | >300 |
| 4 | 50 | 1.1 | 0.5 | 6.4 | 13 | 98% | >300 |

In order to better understand the greater selectivity for HPCMP that was surprisingly found to exist as compared to pressure-driven ultrafiltration, the sieving curve was directly evaluated using available hydrodynamic models for solute convection through porous membranes:

$$S = \phi K_c = \frac{\phi(2 - \phi)K_s}{K_t} \tag{3}$$

where $\phi$ is the equilibrium partition coefficient between the membrane and external solution:

$$\phi = (1-\lambda)^2 \tag{4}$$

and $K_c$ is the hindrance factor for convection, which can be expressed in terms of the functions:

$$K_t = \frac{9}{4}\pi^2 \sqrt{2}(1-\lambda)^{-\frac{5}{2}}\left[1 + \sum_{n=1}^{2} a_n(1-\lambda)^n\right] + \sum_{n=3}^{7} a_n\lambda^n \tag{5a}$$

$$K_s = \frac{9}{4}\pi^2 \sqrt{2}(1-\lambda)^{-\frac{5}{2}}\left[1 + \sum_{n=1}^{2} b_n(1-\lambda)^n\right] + \sum_{n=3}^{7} b_n\lambda^n \tag{5b}$$

where the expansion coefficients $a_n$ and $b_n$ are provided by Bungay and Brenner and summarized in Table 2.

TABLE 2

Expansion Coefficients for the Hydrodynamic Functions $K_t$ and $K_s$

| Subscript n | $a_n$ | $b_n$ |
|---|---|---|
| 1 | −1.2167 | 0.1167 |
| 2 | 1.5336 | −0.0442 |
| 3 | −22.5083 | 4.0180 |
| 4 | −5.6117 | −3.9788 |
| 5 | −0.3363 | −1.9215 |
| 6 | −1.2160 | 4.3920 |
| 7 | 1.6470 | 5.0060 |

Both $K_s$ and $K_t$ are functions of the ratio of the solute radius $r_s$, to the pore radius $r_p$. The solute radius can be expressed in terms of the solute diffusion coefficient using the Stokes-Einstein equation:

$$r_s = \frac{k_b T}{6\pi\mu D} \tag{6}$$

where $k_B$ is Boltzmann's constant, T is the absolute temperature, p is the solution viscosity, and D is the diffusion coefficient. The dextran diffusion coefficient is directly related to the dextran molecular weight (MW) using literature correlations:

$$\log_{10}(D) = -8.1154 - 0.47752 \log_{10}(MW) \tag{7}$$

where D is in $m^2/s$ and MW is in Da. The dashed curve in FIG. 2 is developed using $r_p = 3.7$ nm as determined by eye. The model calculation is somewhat steeper than the experimental data since the model assumes perfectly uniform pore size in contrast to the pore size distribution that is present in the Purema H membrane.

The evaluation of the fractional dextran removal during HPCMP operation is a bit more complicated. The rate of solution diffusion across the hollow fiber membrane can be written as:

$$N_s = \frac{\epsilon \phi K_d D}{\delta_m}(C_b - C_d) \tag{8}$$

where $\phi K_d D$ is the effective solute diffusion coefficient, $\in$ is the membrane porosity, $\delta_m$ is the membrane thickness, and $C_b$ and $C_d$ are the solute concentrations in the bulk (feed) and draw solutions, respectively. The hindrance factor for diffusion ($K_d$) is given as:

$$K_d = \frac{6\pi}{K_t} \tag{9}$$

with $K_t$ given by Equation (3b).

The solution concentration profiles in the hollow fiber module can be evaluated by solving the appropriate mass balances for the bulk and draw solutions accounting for the countercurrent flow. The final equations are equivalent to those developed for countercurrent dialysis, with the fractional removal given as:

$$F = 1 - \frac{C_{retentate}}{C_{feed}} = \frac{1 - \exp(-\beta A)}{\left[1 - \dfrac{\exp(-\beta A)}{\alpha}\right]} \tag{10}$$

where $\alpha$ is the ratio of the draw to feed flow rates:

$$\alpha = \frac{q_D}{q_F} \tag{11}$$

A is the membrane area and $$\beta = \frac{\epsilon \phi K_D D}{\delta_m q_F}\left(1 - \frac{1}{\alpha}\right) \tag{12}$$

The dashed curve in FIG. 2 is the model calculation for the fractional removal using the same membrane pore radius along with the measured membrane area (A=1.9 $m^2$) and membrane thickness ($\delta_m$=30 μm) assuming a membrane porosity of $\in$ =0.4. The model results are in good agreement with the experimental data obtained using HPCMP operation ($q_{feed}$=0.5 ml/min and $q_d$=6.1 ml/min corresponding to α=12.2). The predicted values for the fractional removal rate are somewhat steeper than the experimental results, which is again due to the effects of the pore size distribution on solute transport. The much steeper slope for the fractional removal rate arises from the much stronger dependence of the hindrance factor for diffusion on the ratio of the solute to pore radii as given by the expressions for $K_c$ and $K_d$ (Equations 3 and 9, respectively).

Figure 3:
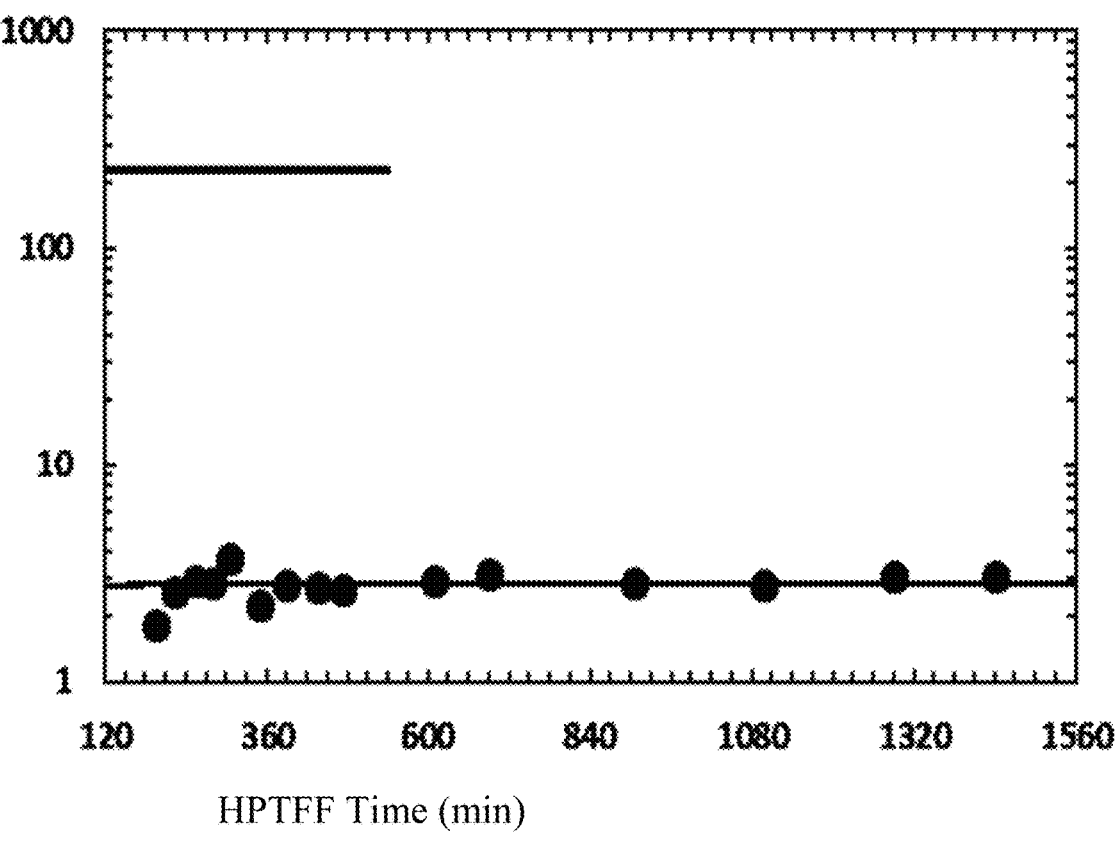
FIG. 3 is a graph illustrating myoglobin (Mb) concentration in the retentate exit compared to total feed concentration for an embodiment of the HPCMP system.

The very steep slope for the fractional removal rate seen in FIG. 2 suggests that it should be possible to use hollow fiber membranes for the separation of proteins with relatively small differences in effective size. Experiments were performed using the model system of BSA and Mb since that protein combination was used in several previous studies of HPTFF. Typical data obtained at a constant feed flow rate of $q_{feed}$=0.5±0.1 mL/min and a draw flow rate of $q_d$=6.1±0.3 mL/min are shown in FIG. 3. The mean transmembrane pressure difference under these conditions was less than 3 kPa throughout the experiment, corresponding to an ultrafiltration rate of less than 0.1 mL/min. The pressure drop across the module (feed inlet minus retentate exit) was also less than 3 kPa due to the very low feed flow rate (0.5 ml/min) used in this experiment; typical hemodialysis is performed using a blood-side flow rate around 300 mL/min. There was no evidence of any membrane fouling over the 24-hr experiment, consistent with previous studies using these hollow fiber membranes for buffer exchange and concentration, both of which were performed at very low filtrate flux.

The results are analyzed in terms of the protein yield:

$$Y_{BSA} = \frac{q_R C_{BSA,R}}{q_{feed} C_{BSA,feed}}$$

$$Y_{Mb} = \frac{q_D C_{Mb,D}}{q_{feed} C_{Mb,feed}}$$

and purification factor:

$$P = \frac{\left(C_{BSA,R}/C_{Mb,R}\right)}{\left(C_{BSA,feed}/C_{Mb,feed}\right)}$$

with the BSA and Mb concentrations determined by UV absorbance. The BSA yield was >98% throughout the experiment; there was no measurable amount of BSA in any of the draw samples. The Mb yield in the draw increased with time at the start of the experiment as the buffer was washed out of the shell region of the hollow fiber module, approaching a value above 98.5% after about 3 hr of operation. The purification factor for BSA was greater than 80-fold due to the high degree of Mb removal. It was not possible to evaluate the purification factor for myoglobin in the draw solution because the BSA concentration was below the limit of quantification. This corresponds to $P_{Mb} \geq 300$ based on a BSA detection limit of 0.01 g/L.

Figure 4:
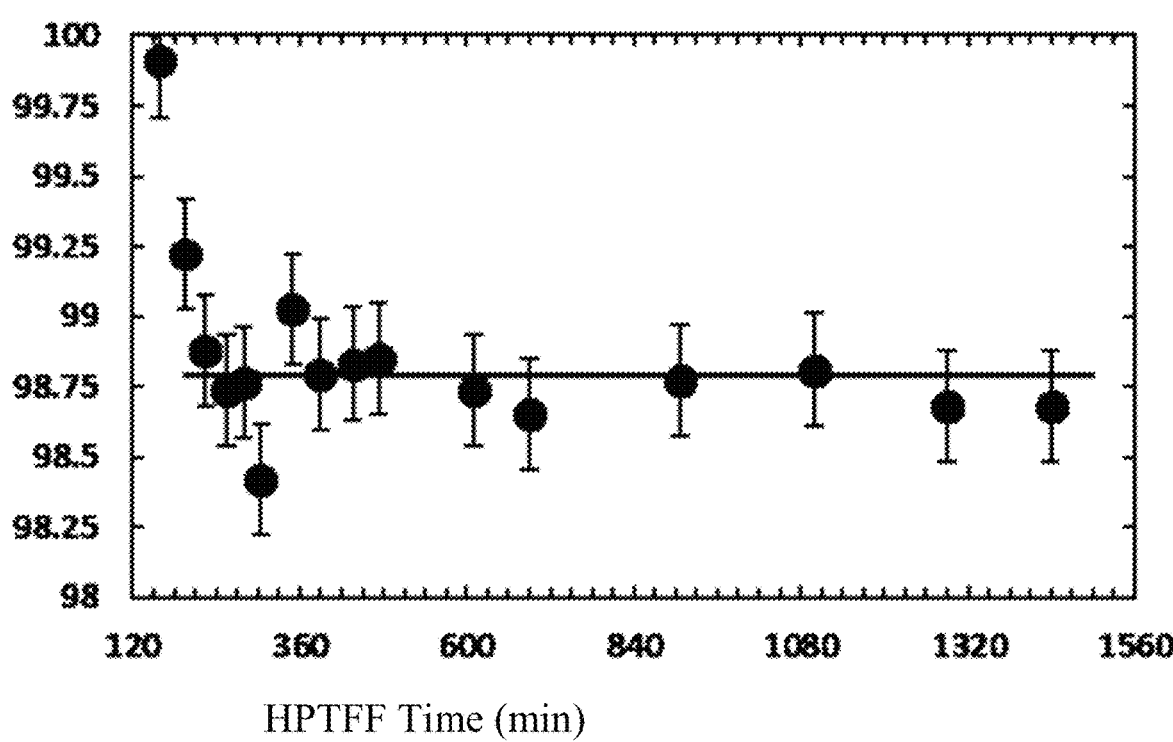
FIG. 4 is a graph illustrating the percentage removal of myoglobin (Mb) represented as the experimental impurity for an embodiment of the HPCMP system.
Figure 5A:
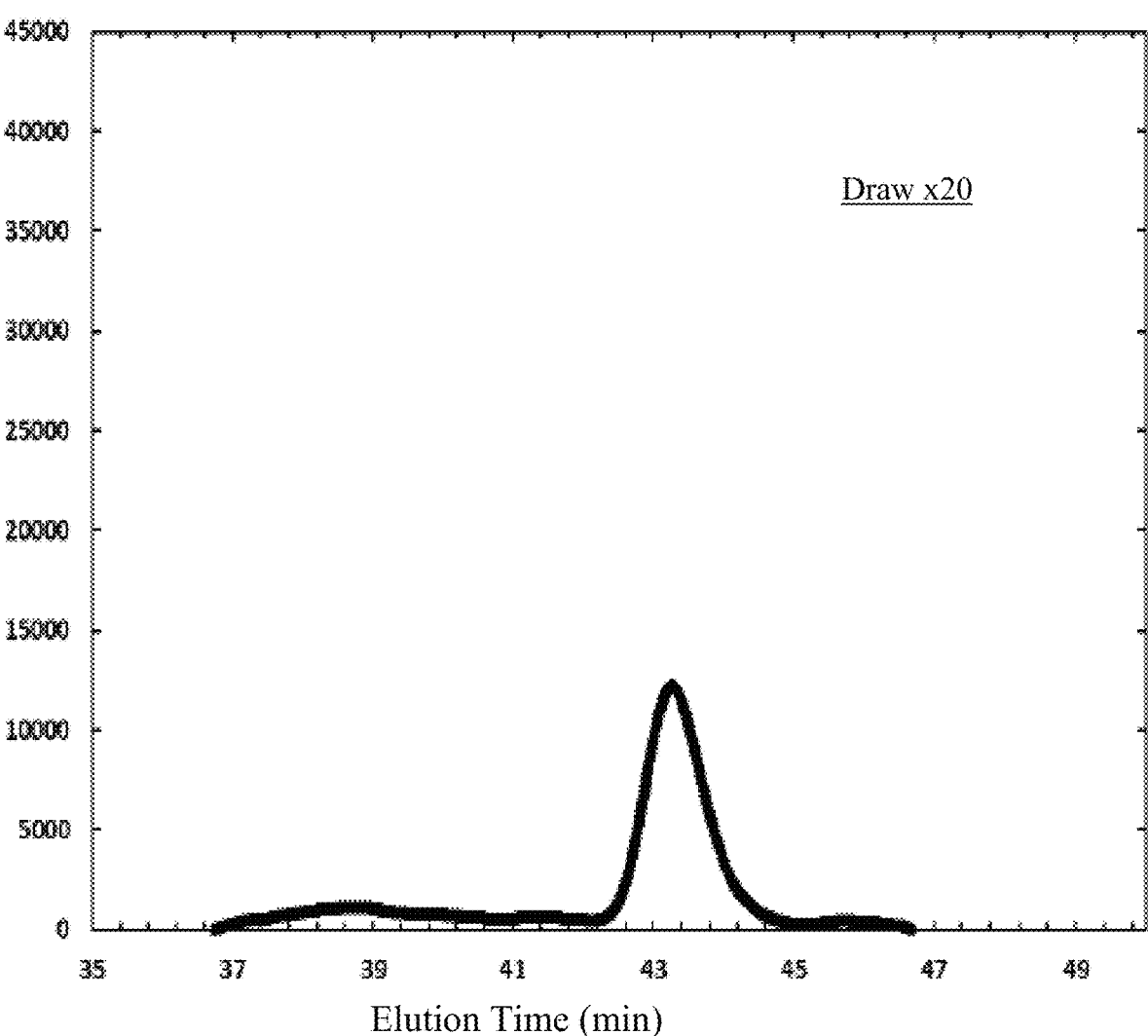
FIG. 5a is a graph illustrating high-performance liquid chromatography (HPLC) analysis results of a draw sample.
Figure 5B:
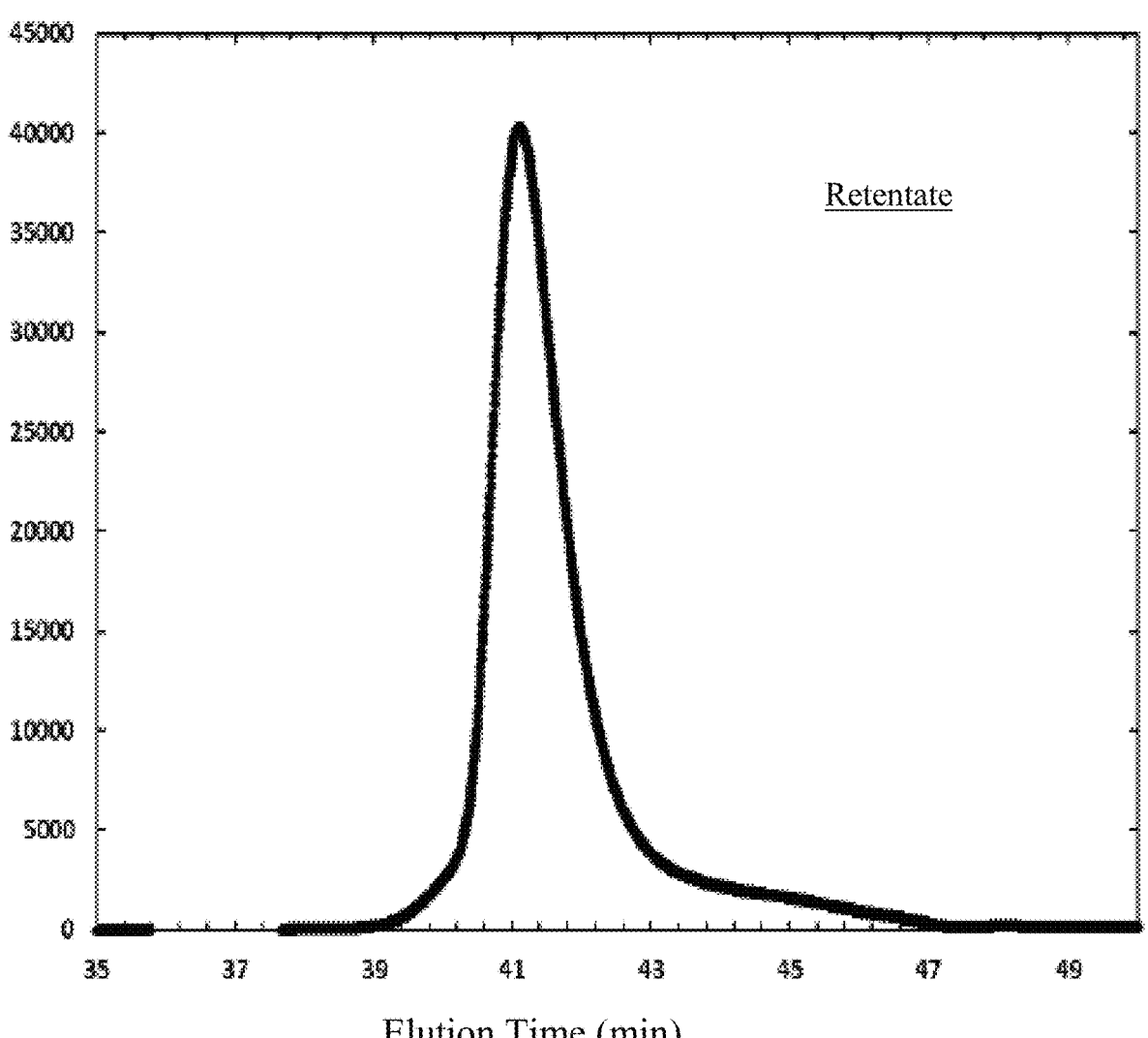
FIG. 5b is a graph illustrating high-performance liquid chromatography (HPLC) analysis results of a retentate sample.
Figure 5C:
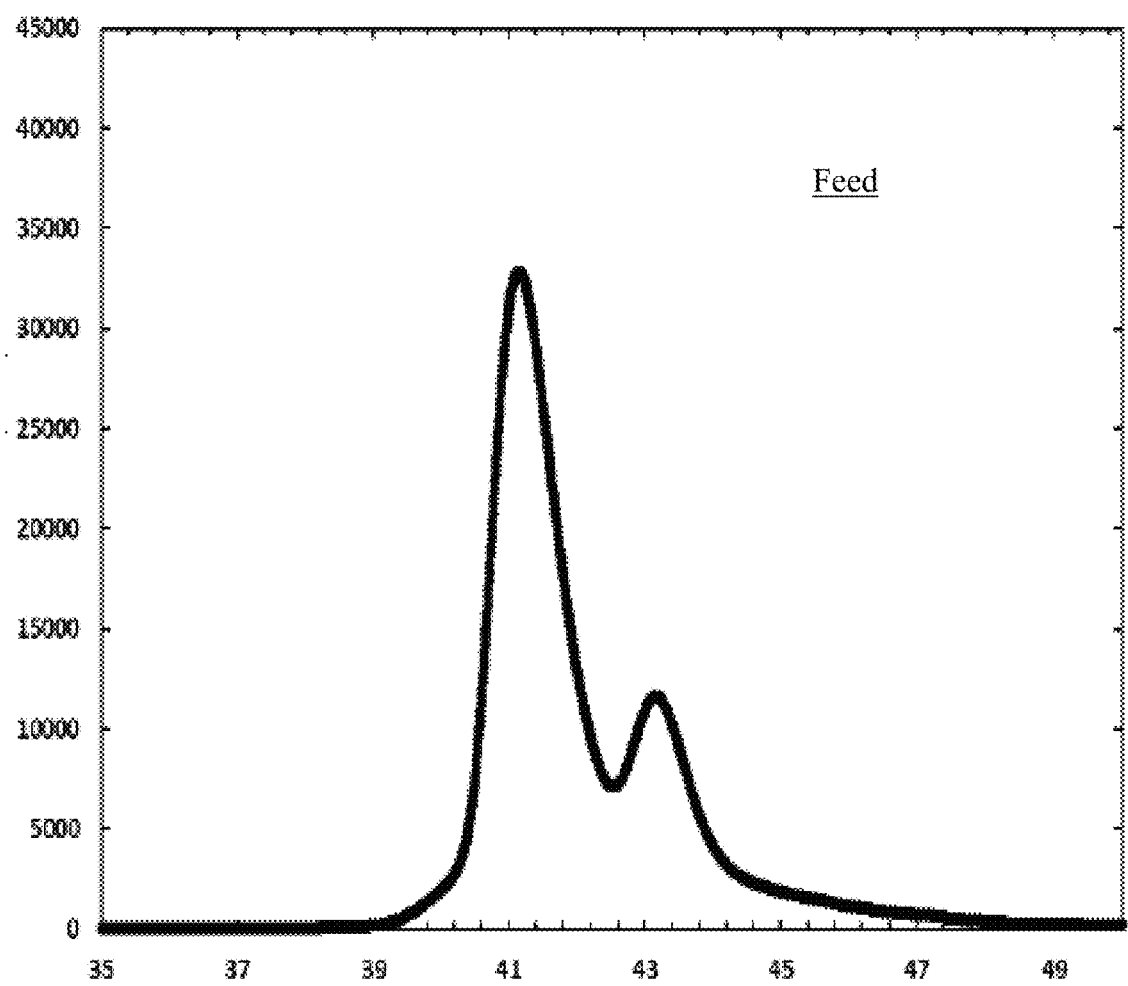
FIG. 5c is a graph illustrating high-performance liquid chromatography (HPLC) analysis results of a feed sample.

In order to confirm the high degree of purification seen in FIGS. 3-4, samples were collected from the feed, draw, and retentate exit lines towards the end of each experiment and analyzed by HPLC as shown in FIGS. 5a-5c. The feed shows two distinct peaks centered at 41 and 43 minutes, corresponding to BSA and Mb, respectively. The retentate sample shows a large BSA peak with a "tail" at longer times which is likely associated with the presence of a small amount of Mb. The draw solution shows only a single peak corresponding to Mb with no evidence of any BSA.

Figure 6:
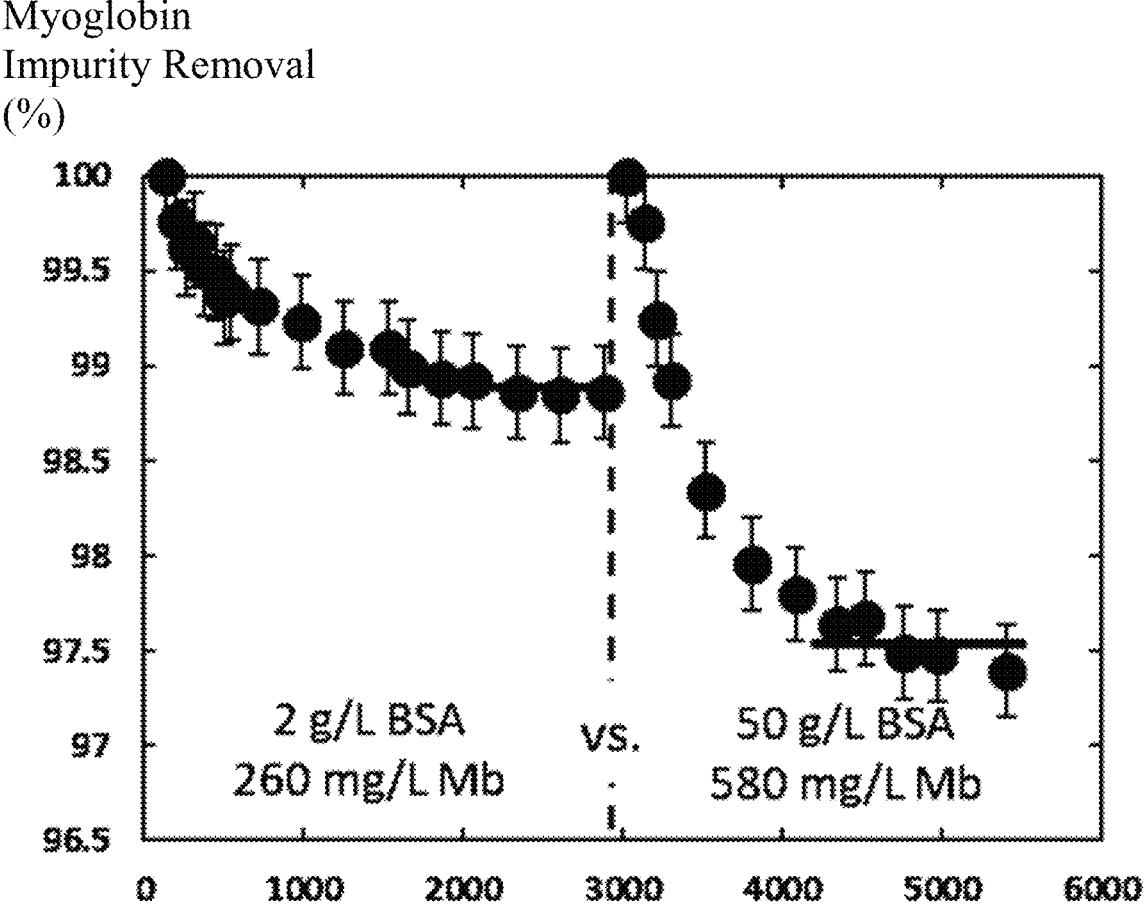
FIG. 6 is a graph illustrating the percentage removal of myoglobin (Mb) represented as the experimental impurity for two different feed concentration conditions for an embodiment of the HPCMP system.

One of the potential advantages of HPCMP is that the predicted performance should be relatively independent of the feed concentrations for either the product or impurity. This is in sharp contrast to pressure-driven TFF processes in which high concentrations lead to low filtrate flux due to the build-up of a highly concentrated region of retained solutes at the membrane surface. In order to confirm this result, a subsequent experiment was performed at much higher protein concentrations: $C_{Mb}$=560 mg/L and $C_{BSA}$=50 g/L. The experiment was performed in 2-stages, beginning with a dilute feed solution (2 g/L BSA) for the first 24 hr and then switching to the 50 g/L BSA solution for the next 24 hr. Results over the entire 48 hr experiment are shown in FIG. 6. There was again no detectable BSA in the draw exit under any conditions, even when using the 50 g/L BSA. This corresponds to a Mb purification factor of more than 1000-fold. The extent of BSA purification was nearly 100-fold in the dilute solution, but this dropped to closer to 50-fold at the higher BSA concentration. This is likely due to non-ideal effects in the concentrated protein solution.

The data presented in this first set of experiments provided a demonstration of HPCMP for the separation of an exemplary model protein system. Data obtained with BSA and Mb showed nearly 100% yield of both proteins with purification factors of Mb and BSA of >500-fold and nearly 100-fold, respectively, with stable performance over more than 24 hr of continuous separation. Note that previous studies of BSA-Mb separation using pressure-driven membrane separations (HPTFF) reported a maximum selectivity of only 14.2, and this still required the use of specially-designed negatively-charged membranes made with sulfonic-acid modified carbon nanotubes. Data obtained with conventional ultrafiltration membranes (without the carbon nanotubes) showed a maximum selectivity of less than 7-fold, which is nearly 100 times smaller than the selectivity obtained in the HPCMP experiments in the first set of experiments.

The high selectivity that can be provided in HPCMP embodiments was confirmed using dextran transport measurements obtained with the same membrane module but operated using either pressure-driven filtration or countercurrent diffusion. Results for the HPCMP system showed much greater selectivity than that for the pressure-driven filtration, which is consistent with theoretical calculations performed using available hydrodynamic models for solute convection and diffusion across porous membranes.

Another unique and surprising advantage of embodiments of the HPCMP system that can be understood from the first set of experiments is that the HPCMP module can be configured to effectively operate continuously with only a single pump pass. In contrast, previous studies of pressure-driven HPTFF were performed using batch diafiltration, with the retained product recirculated through the membrane module (and the feed pump) more than 100 times during the process. This repeated pumping can reduce product quality, e.g., through the formation of protein aggregates, an effect that should be negligible in HPCMP utilizing only a single pump pass. The ability to operate HPCMP continuously provides exciting opportunities for use of this technology as part of fully-integrated continuous processes for biopharmaceutical manufacturing. The potential advantages of continuous bioprocessing that can be provided via embodiments of the HPCMP module can include lower capital and operating costs, increased manufacturing flexibility, and greater speed to market.

Exemplary Model Development

Exemplary process optimization equations and diagrams describing the tradeoff between yield and purification factor for embodiments of HPCMP processes we developed are further discussed below. Exemplary model equations were developed based on the classical description of countercurrent contactors, with the magnitude of the selectivity further analyzed using available models for hindered diffusion through porous membranes accounting for the effects of a pore size distribution. The results of our exemplary model development provide insights into the factors controlling the performance of HPCMP for different embodiments as well as proving an exemplary framework for the design and optimization of embodiments of the HPCMP processes that can be used for bioprocessing applications as well as other processing applications (e.g. natural protein product separations including dairy products, whey proteins, egg proteins, and plasma proteins that can be utilized in conjunction with dairy processing, food production, or other types of animal protein processing).

Figure 7:
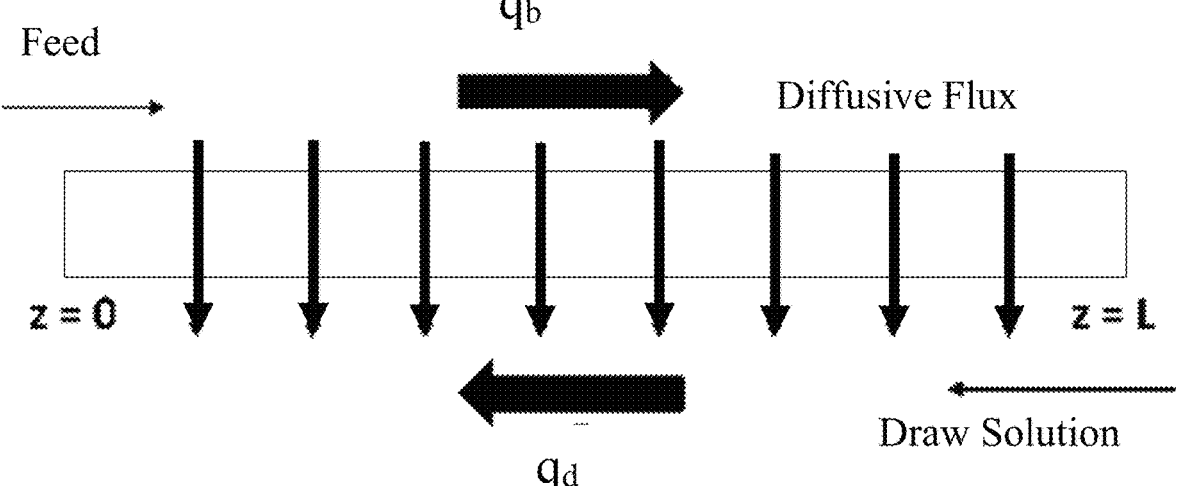
FIG. 7 is a schematic view of an exemplary HPCMP process, which illustrates separation accomplished by differences in diffusive flux across a semi-permeable membrane.

As discussed above, HPCMP can be performed using countercurrent contacting, with the separation accomplished by differences in diffusive flux across a semi-permeable membrane as shown schematically in FIG. 7. For simplicity, the feed is assumed to contain a binary mixture of the product and a single impurity, denoted as solutes 1 and 2, with a draw solution, containing only the buffer of interest, introduced in a countercurrent fashion on the other side of the membrane.

The solute concentration can be evaluated as a function of position (z) by solving the area-averaged mass balances for the bulk and draw solutions (Eloot, 2004):

$$q_b \frac{dC_b}{dz} = -k_o a[C_b - C_d] \tag{13}$$

$$q_d \frac{dC_d}{dz} = -k_o a[C_b - C_d] \tag{14}$$

where $q_b$ and $q_d$ are the volumetric flow rates in the bulk and draw solutions, $C_b$ and $C_d$ are the protein concentrations, $k_o$ is the overall mass transfer coefficient (directly related to the effective protein diffusion coefficient through the membrane), and a is the membrane area per unit length. Equations (13) and (14) can be integrated over the length of the membrane to evaluate the ratio of the protein concentration exiting the HPCMP system in the bulk solution ($C_{b,z=L}$) relative to that in the inlet ($C_{b,z=o}$):

$$\frac{C_{b,z=L}}{C_{b,z=0}} = \frac{\alpha - 1}{\alpha \exp(\beta) - 1} \tag{15}$$

where $\alpha$ is the ratio of the draw to bulk solution flow rates:

$$\alpha = \frac{q_d}{q_b} \tag{16}$$

and $\beta$ provides a measure of the mass transfer efficiency:

$$\beta = \frac{k_o a L}{q_b} \left(1 - \frac{1}{\alpha}\right) \tag{17}$$

For the protein that is primarily retained by the membrane (solute 1), the yield and purification factor become:

$$Y_1 = \frac{C_{b,z=L}}{C_{b,z=0}} = \frac{\alpha - 1}{\alpha \exp(\beta_1) - 1} \tag{18}$$

-continued $$P_1 = \frac{Y_1}{Y_2} = \frac{\alpha\exp(\beta_2) - 1}{\alpha\exp(\beta_1) - 1} \tag{19}$$

where the subscripts 1 and 2 refer to the product (e.g. first protein) and impurity (e.g. the second protein), respectively (less and more permeable species). Note that the volumetric flow rates in Equations (18) and (19) drop out of the analysis since the bulk solution flow rates at the inlet and outlet are equal due to the assumption of negligible convective transport across the membrane. These equations can be combined to develop an expression for the purification factor as an explicit function of the yield $$P_1 = \frac{\alpha Y_1 \left[\frac{\alpha - 1 + Y_1}{\alpha Y_1}\right]^{\psi} - Y_1}{\alpha - 1} \tag{20}$$

where the selectivity is defined as:

$$\psi = \frac{\beta_2}{\beta_1} = \frac{k_{o2}}{k_{o1}} \tag{21}$$

The corresponding equations for the product collected in the draw solution are:

$$Y_2 = \frac{q_d C_{d,exit}}{q_b C_{b0}} = \frac{\alpha[\exp(\beta_2) - 1]}{\alpha\exp(\beta_2) - 1} \tag{22}$$

$$P_2 = \frac{Y_2}{Y_1} = \frac{[\exp(\beta_2) - 1][\alpha\exp(\beta_1) - 1]}{[\exp(\beta_1) - 1][\alpha\exp(\beta_2) - 1]} \tag{23}$$

Equations (22) and (23) can again be combined into a single equation for the purification factor as a function of the yield, with $\alpha$ and $\psi$ as the two parametric variables, although the resulting expression is algebraically messy and is not shown.

Figure 8:
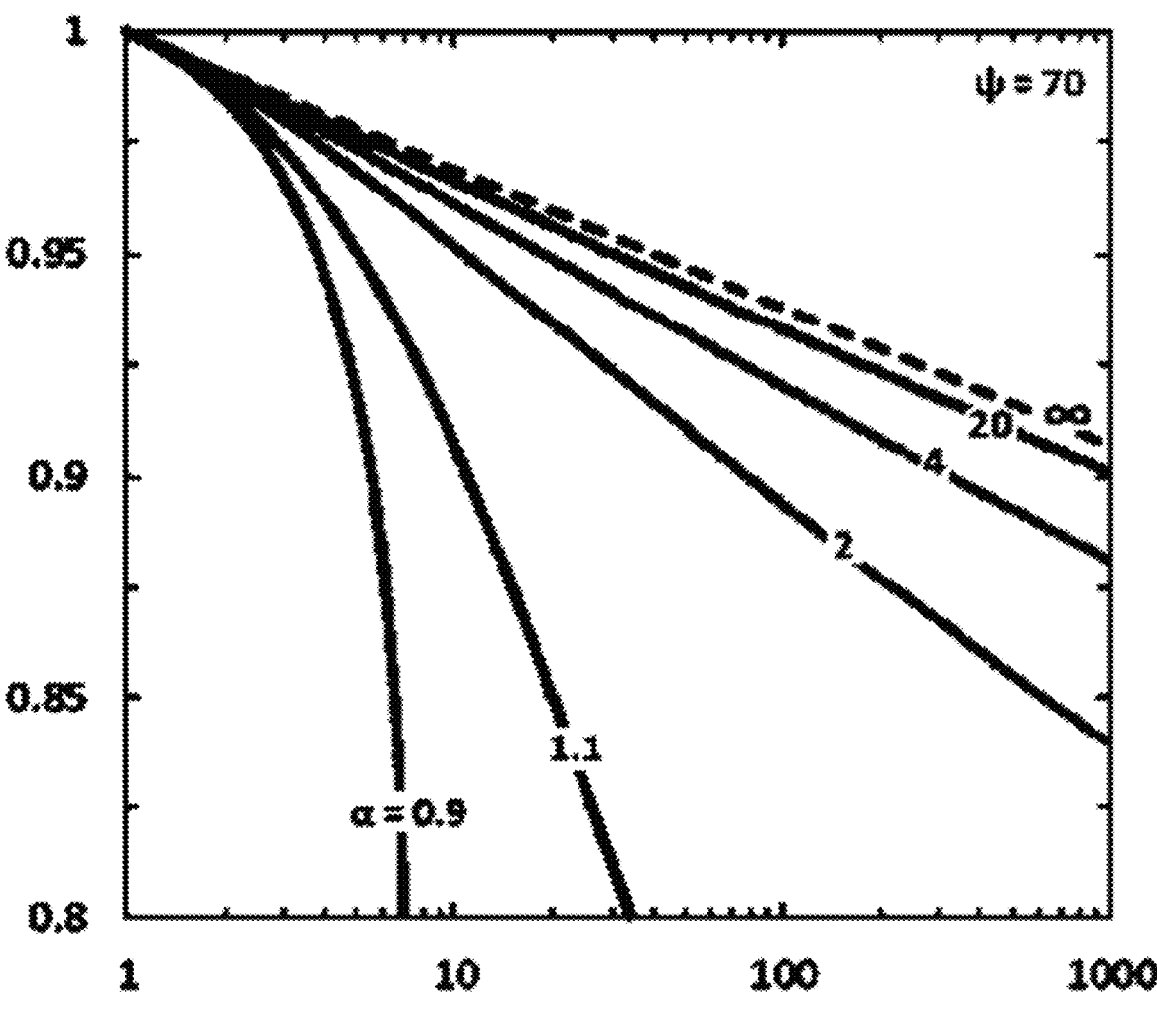
FIG. 8 is a graph illustrating yield (Yield, $Y_1$) as a function of the purification factor ($P_1$) for a first product collected in a bulk solution for different ratios of the draw to feed flow rates ($\alpha$) at a selectivity of $\psi$=70.

FIG. 8 shows a plot of the yield as a function of the purification factor for a product collected in the bulk solution for different values of $\alpha$ at a selectivity of $\psi=70$, which is the value previously determined for the separation of myoglobin and bovine serum albumin by HPCMP in Example 1. Results are only shown for $Y_1 \geq 0.8$ since this is the region of primary interest for industrial applications. The dashed line shows results for the maximum yield, which is given by Equation (20) in the limit of $\alpha \to \infty$:

$$P_1 = Y_1^{1-\psi} \tag{24}$$

Note that Equation (24) is identical to the expression for HPTFF but with the selectivity given by the ratio of the protein sieving coefficients instead of the ratio of the protein mass transfer coefficients. The equivalence in performance under these conditions arises because $C_d \to 0$ at very large $\alpha$, with the solute flux becoming directly proportional to $C_b$ for both HPCMP and HPTFF.

A module with very small membrane area would give results near the upper left-hand corner of FIG. 8, beginning at $Y_1=1$ and $P_1=1$ in the limit as $A \to 0$ since there would be no transport across the membrane under these conditions. Increasing the membrane area allows for high levels of removal of the more permeable impurity, although there is a corresponding loss of product due to diffusion across the semi-permeable membrane. A membrane with $\psi=70$ is able to provide 1000-fold purification with more than 90% yield for $\alpha \geq 20$. The product yield at a given purification factor increases with increasing values of $\alpha$ due to the more effective removal of the impurity into the draw solution. For example, the product yield at $P_1=100$ increases from $Y_1=0.70$ for $\alpha=1.1$ to more than 0.92 for $\alpha=20$. However, the change in yield becomes relatively small for $\alpha \geq 4$, which would make it difficult to justify the additional buffer consumption required to operate at these high values of $q_d$.

Figure 9:
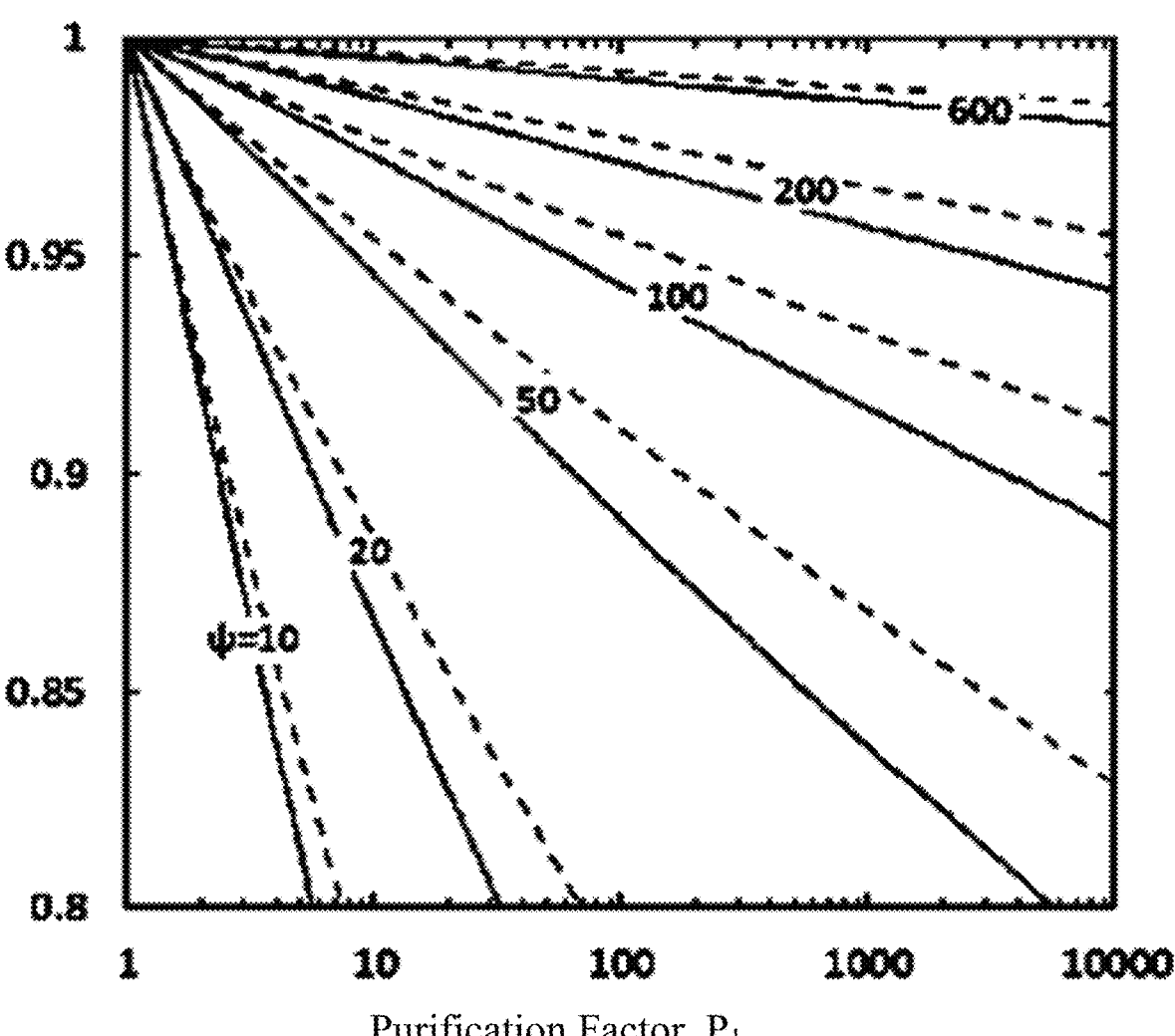
FIG. 9 is a graph illustrating the yield-purification tradeoff for the first product collected in a bulk solution at several values of the selectivity ($\psi$) for $\alpha$=4 (solid lines) and $\alpha$=∞ (dashed lines) for the first product.

FIG. 9 shows the yield-purification factor tradeoff for a product collected in the bulk solution at several values of the selectivity for $\alpha=4$ (solid curves) and $\alpha=\infty$ (dashed curves), with the latter providing the maximum possible yield at a given purification factor. Again, there is relatively little difference between the results at the two values of $\alpha$, although the difference between the curves is slightly greater at intermediate values of the selectivity. High performance separations ($P_1 \geq 100$ with $Y_1 \geq 0.9$) require a selectivity of at least 50 using $\alpha=4$, while it is theoretically possible to achieve a purification factor of 1000-fold with 95% yield using a membrane that provides $\psi \geq 170$.

Figure 10:
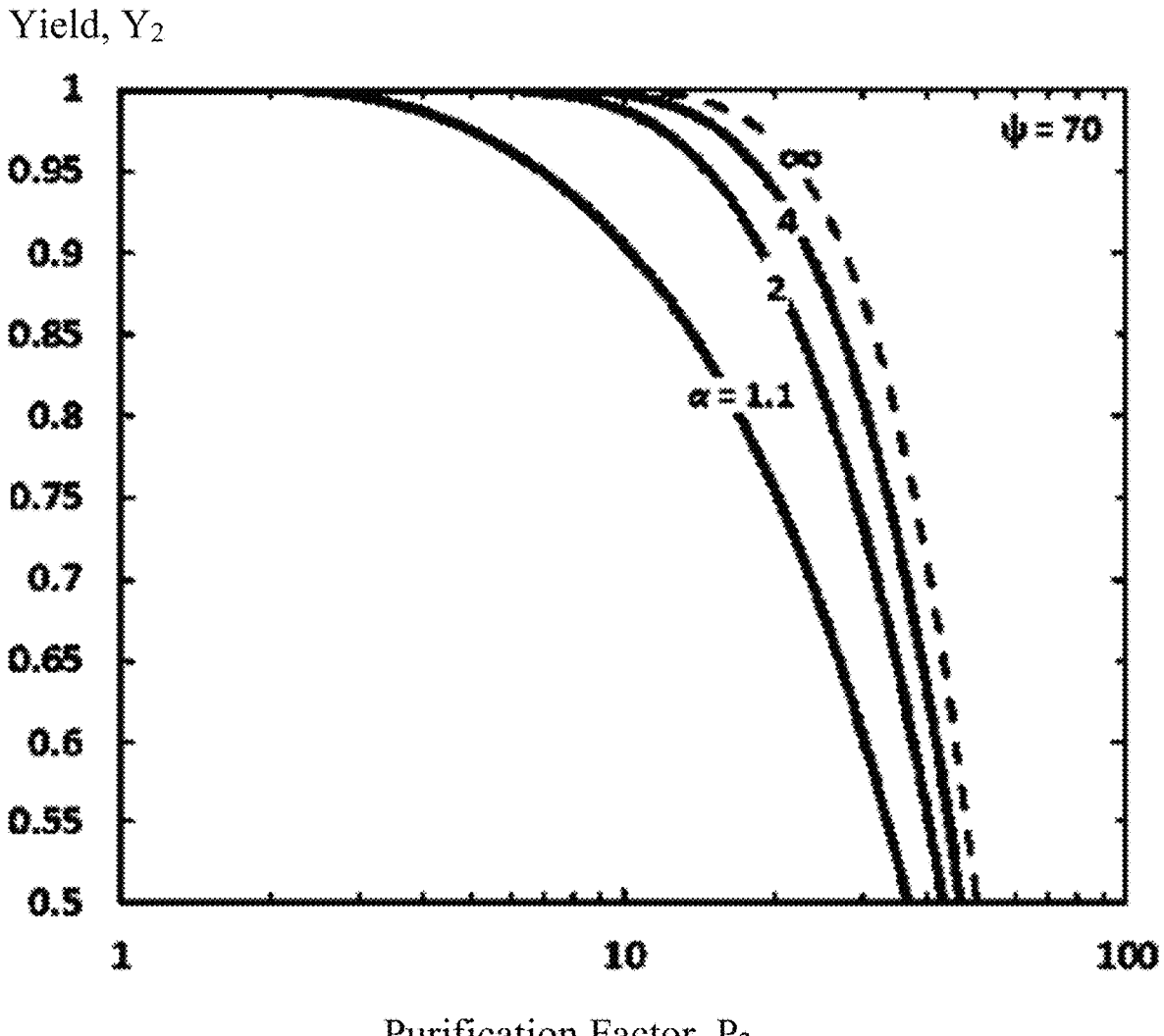
FIG. 10 is a graph illustrating yield (Yield, $Y_2$) as a function of the purification factor ($P_2$) for a second product collected in a bulk solution for different ratios of the draw to feed flow rates ($\alpha$) at a selectivity of $\psi$=70.
Figure 11:
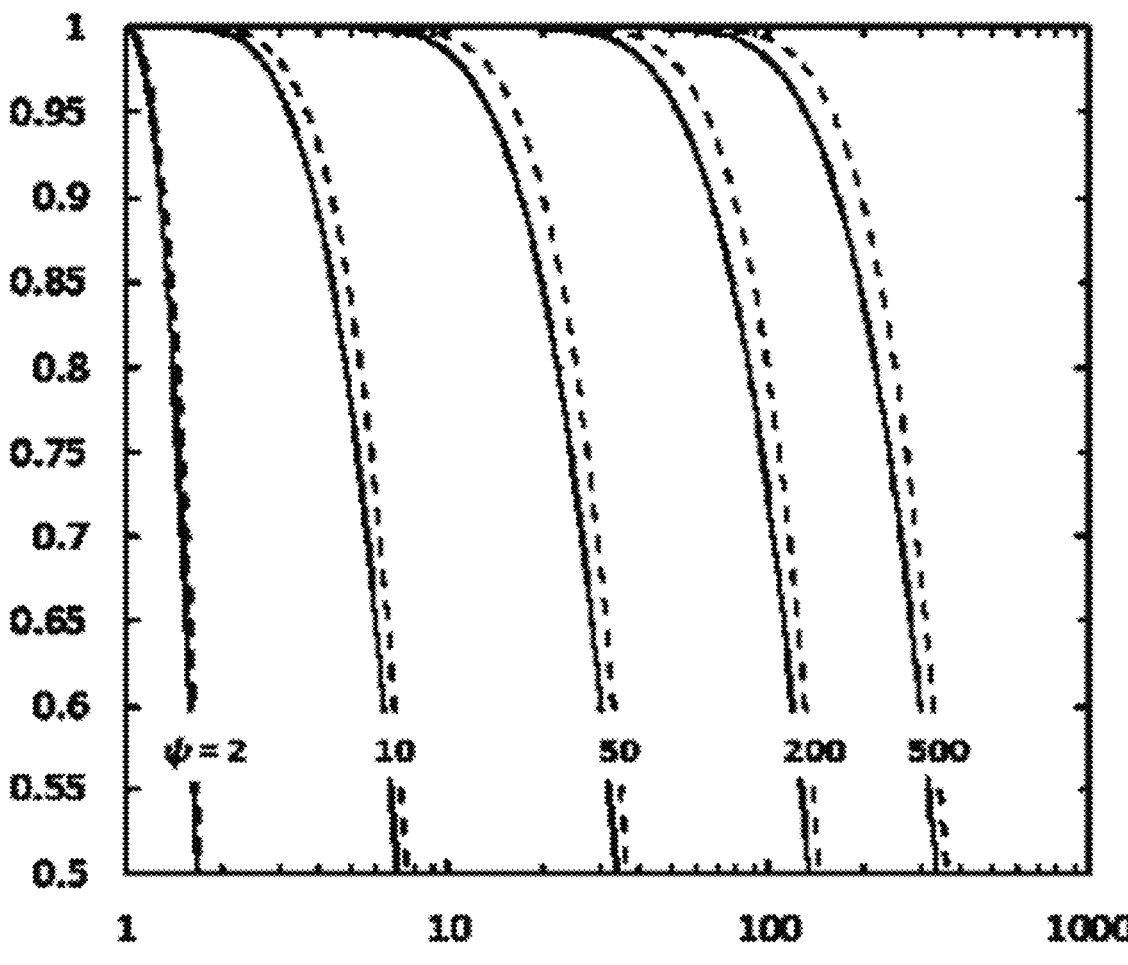
FIG. 11 is a graph illustrating the yield-purification tradeoff for the second product collected in the bulk solution at several values of the selectivity ($\psi$) for $\alpha$=4 (solid lines) and $\alpha$=∞ (dashed lines).

Corresponding results for a product collected in the draw solution are shown in FIGS. 10 and 11. In this case, a module with very little membrane area would provide the maximum purification factor but with minimal yield (the lower right corner of the process optimization diagram) since very little product (or impurity) would be collected in the draw solution under these conditions. Increasing the membrane area would allow one to increase the product yield, but with a corresponding loss in purification due to the diffusive flux of impurity across the membrane. The product yield increases with increasing $\alpha$ since this increases the driving force for diffusion into the draw solution, although this also leads to a more dilute product. The dashed curve represents the maximum attainable yield, which again occurs as $\alpha \to \infty$. Under these conditions, the purification factor—yield relationship can be developed directly from Equations (22) and (23) giving:

$$P_2 = \frac{Y_2}{1 - (1 - Y_2)^{1/\psi}} \tag{25}$$

Equation (25) is again equivalent to the expression for the purification-yield tradeoff in HPTFF for a product collected in the permeate (Van Reis and Saksena, 1997).

FIG. 11 shows the trade-off between yield and purification factor for a product collected in the draw solution at different values of the selectivity. Much higher selectivity is required to achieve the same performance as that for a product in the bulk solution. For example, the conditions of $P_2=100$ with $Y_2=0.9$ requires $\psi \geq 290$ for $\alpha=4$ for a product in the draw solution compared to only $\psi=55$ for a product in the bulk. Again, there is relatively little difference between the results at $\alpha=4$ and those with $\alpha=\infty$. In this case, the larger value of $\alpha$ would not only increase the buffer requirements, it would also increase the dilution of the product of interest.

Since protein mass transfer is likely limited by diffusion across the membrane, as opposed to mass transfer in the bulk/draw solutions, the selectivity for the HPCMP process (Equation 21) will be approximately equal to the ratio of the diffusion coefficients of the product and impurity through the membrane:

$$\psi = \frac{D_2}{D_1} = \frac{(\phi K_d D_\infty)_2}{(\phi K_d D_\infty)_1} \tag{26}$$

where $D_1$ and $D_2$ are the protein diffusivities in the membrane and $D_{\infty 1}$ and $D_{\infty 2}$ are the corresponding diffusivities in free solution, which can be evaluated using the Stokes-Einstein equation for diffusion of a hard sphere of radius $r_i$:

$$D_{\infty,i} = \frac{k_B T}{6\pi\eta r_i} \tag{27}$$

where $k_B$ is the Boltzmann constant, T is the absolute temperature, and $\eta$ is the solvent viscosity. $\phi$ is the equilibrium partition coefficient for the protein between the membrane pores and the external solution immediately adjacent to the membrane:

$$\phi = (1-\lambda)^2 \tag{28}$$

which is a function of the ratio of the protein to pore radii, $\lambda = r_s/r_p$. $K_d$ is the hindrance factor for diffusion, which has been evaluated by Bungay and Brenner (Bungay and Brenner, 1973) based on solution of the Navier-Stokes equation for flow of a sphere in a closely-fitting cylinder giving:

$$K_d = \frac{6\pi}{K_t} \tag{29}$$

$$K_t = \frac{9}{4}\pi^2\sqrt{2}(1-\lambda)^{-\frac{5}{2}}\left[1+\sum_{n=1}^{2}a_n(1-\lambda)^n\right]+\sum_{n=3}^{7}a_n\lambda^n \tag{30}$$

with the expansion coefficients $a_n$ given in Table 2 (provided above).

Model calculations were performed for membranes with a log normal pore size distribution:

$$f(r_p) = \frac{1}{r_p\sqrt{2\pi b}}\exp\left[\frac{-\left(\text{Log}\left[\frac{r_p}{\bar{r}}\right]+\frac{b}{2}\right)^2}{2b}\right] \tag{31}$$

where $\bar{r}$ is the mean pore radius and b is a function of the standard deviation ($\sigma$):

$$b = \text{Ln}[1+\sigma^2] \tag{32}$$

The effective diffusivity was then evaluated by integration over the pore size distribution:

$$\frac{D_1}{D_{\infty,1}} = \frac{\int_{r_1}^{\infty} f(r_p)\phi(r_p)K_d(r_p)r_p^2 dr_p}{\int_{0}^{\infty} f(r_p)r_p^2 dr_p} \tag{33}$$

where $D_{\infty,1}$, $\phi$, and $K_d$ are all evaluated with $r_s = r_1$. The selectivity is then evaluated directly from Equation (26) using the corresponding expression for $D_2$.

Figure 12:
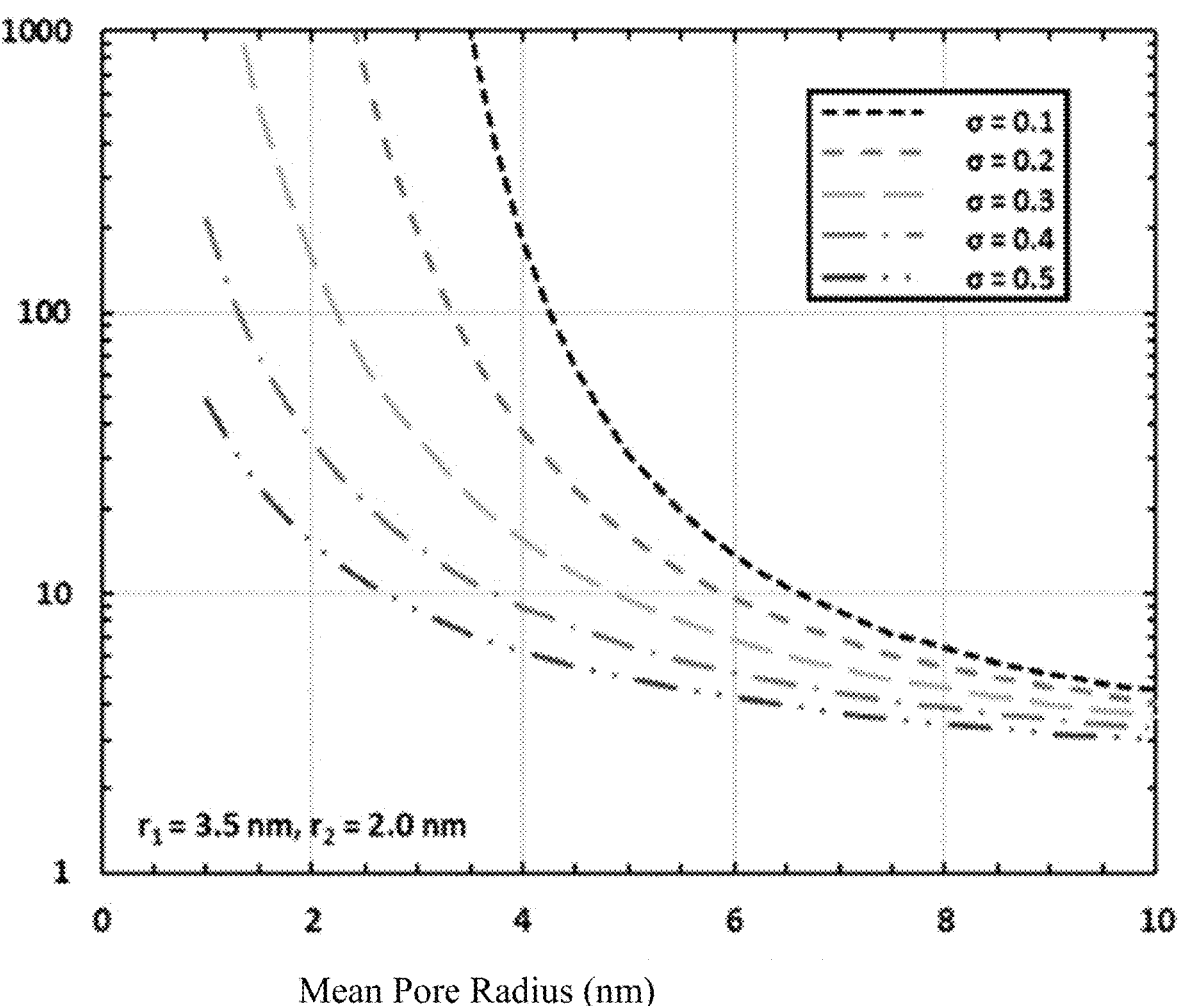
FIG. 12 is a graph illustrating the effect of the mean pore radius and the coefficient of variation ($\sigma$) on the selectivity for the separation of proteins including a first protein with a protein radius $r_1$ of 3.5 nm and a second protein with a protein radius $r_2$ of 2.0 nm. The coefficient of variation ($\sigma$) is equal to the ratio of the standard deviation in the pore size distribution to the mean pore size.

FIG. 12 shows the effects of the mean pore radius and the coefficient of variation (equal to the ratio of the standard deviation to the mean) for the separation of proteins with $r_1 = 3.5$ nm and $r_2 = 2.0$ nm, which are the approximate hydrodynamic radii of BSA and myoglobin, respectively. For a given mean pore radius, the selectivity increases with decreasing standard deviation, i.e., as the pore size distribution becomes narrower. The selectivity also increases significantly as the mean radius is reduced since this causes a much greater reduction in $D_1$ than $D_2$ due to the strong dependence of the hindrance factor for diffusion on the protein radius. However, this decrease in the protein diffusion coefficient means that one would need to operate with either very large membrane area or at a very low flow rates to provide sufficient residence time within the module for effective transport of the smaller impurity into the draw solution. Previous studies indicate that commercial ultrafiltration membranes tend to have coefficient of variation around 0.2; thus, a selectivity of 100 could be achieved for the BSA-myoglobin separation using a membrane with a mean pore radius of 3.2 nm, which is just smaller than the size of the larger BSA. It is important to note that these calculations assume that the separation is governed entirely by the physical size of proteins and membrane pores, which ignores possible contributions from electrostatic interactions between the proteins and membrane.

The performance of HPCMP and HPTFF are compared directly in Table 3 for the separation of a model protein mixture with $r_1 = 3.5$ nm and $r_2 = 2.0$ nm; similar results were obtained with other protein mixtures and with membranes having different pore size distributions. In particular, selectivities and purification factors (at 90% yield) for HPCMP and HPTFF with separation of proteins with $r_1 = 3.5$ nm and $r_2 = 2.0$ nm using a membrane with mean pore radius of 1.5 nm for the results shown in Table 3.

TABLE 3

| Selectivity Comparison Between Embodiments of HPCMP and HPTFF | | | | | | |
|---|---|---|---|---|---|---|
| Coefficient of | Selectivity, $\psi$ | | Purification Factor (bulk, $P_1$ at $Y_1 = 0.9$) | | Purification Factor (draw, $P_2$ at $Y_2 = 0.9$) | |
| Variation ($\sigma/\bar{r}$) | HPCMP | HPTFF | HPCMP | HPTFF | HPCMP | HPTFF |
| 0.175 | 2060 | 185 | $1.8 \times 10^{71}$ | $7.5 \times 10^{49}$ | 680 | 73 |
| 0.2 | 543 | 56 | $6.9 \times 10^{18}$ | 330 | 178 | 22 |
| 0.225 | 208 | 25 | $1.8 \times 10^7$ | 12 | 68 | 10 |
| 0.25 | 100 | 13 | 3421 | 4 | 33 | 6 |
| 0.275 | 58 | 9 | 120 | 2.3 | 20 | 4 |

Model calculations were performed for a membrane with $\bar{r} = 1.5$ nm for several values of the coefficient of variation (($\sigma/\bar{r}$). The selectivity for HPCMP was evaluated using Equations (26) and (33). The corresponding values for HPTFF were determined by a similar integration over the pore size distribution using the expressions for the sieving coefficient given by Mochizuki and Zydney (1993). The selectivity increases as the coefficient of variation decreases due to the reduction in the breadth of the pore size distribution. In each case, the selectivity for HPCMP was significantly greater than that for HPTFF, which is a direct result of the strong dependence of the hindrance factor for diffusion on the protein size. In contrast, the hindrance factor for convection is nearly independent of the protein radius.

The greater selectivity in HPCMP compared to HPTFF that was surprisingly found to exist for embodiments of HPCMP leads to a significantly higher degree of purification for the products obtained in both the bulk and draw solutions (with the calculations for HPCMP performed with $\alpha=4$ based on the results in FIGS. 8 to 11). This is particularly true for small values of $\sigma/\bar{r}$ where the model predicts extremely large values for the purification factor; such processes would easily enable much higher yields than the $Y=0.9$ used in Table 3. The results in Table 3 indicate that commercially available ultrafiltration membranes with $\sigma/\bar{r}\approx0.2$ can readily achieve the high degrees of purification required in bioprocessing using HPCMP for products in both the bulk and draw solutions based solely on differences in size. Note that a membrane with $\sigma/\bar{r}=0.225$ would be nearly useless for protein purification by HPTFF (purification factors $\leq13$) but could potentially provide more than a million-fold purification of a product in the bulk solution using HPCMP (with $P=69$ for the product in the draw solution). In addition, HPCMP with $\alpha=4$ will use significantly less buffer than HPTFF since HPTFF typically requires at least 10 diavolumes, and in some cases more than 20 diavolumes, for effective protein purification where 10 diavolumes would correspond to a buffer volume that is 10× the feed volume.

As discussed herein, we have developed as a new approach for purification of proteins and other biotherapeutics (e.g., pegylated proteins, antibody-drug conjugates, glycoconjugate vaccines) that can be implemented in embodiments of HPCMP, which was surprisingly found to be able to exploit highly selective diffusive transport for separation of proteins with relatively small differences in size. The quantitative process optimization equations and diagrams provided herein that describe the inherent trade-off between the product yield and purification factor in terms of two key parameters: the selectivity (equal to the ratio of the mass transfer coefficients of the proteins of interest) and the ratio of the draw to bulk solution flow rates can facilitate development of an optimized embodiment for a particular application. For example, the process optimization diagrams and equations we developed can allow one to rapidly identify conditions required for high yield/high purification factor separations. In addition, the results in our exemplary model development suggest that operation at ratios of draw to bulk solution flow rates of $\alpha\geq4$ is unlikely to be attractive for most applications given the relatively small increase in product yield at the cost of much higher buffer consumption. While this result is suggested, it is contemplated that use of greater value of a can still be suitable for various commercial applications for some embodiments as well.

As discussed above, exemplary model simulations were also used to evaluate the effect of the membrane pore size distribution on the selectivity for purely size-based separations. The results show that existing membranes (i.e., membranes characterized by a log-normal pore size distribution with coefficient of variation equal to 0.2), are able to provide selectivity of $\psi\geq100$ even for proteins that differ by less than a factor of two in radius. This diffusive selectivity is significantly greater than the selectivity that can be achieved using more traditional pressure-driven filtration (HPTFF) due the strong dependence of the hindrance factor for diffusion on the solute radius. In addition, HPCMP uses less buffer than HPTFF and it can be performed as a truly continuous process operating at steady-state.

It is important to note that the tradeoff between yield and purification factor described by the process optimization diagrams provided herein is independent of the membrane area or thickness. Instead, the area defines the trajectory along a curve at constant selectivity and flow ratio. However, the use of a thinner membrane would provide a shorter diffusive path length across the membrane. This would reduce the membrane area needed for the separation (operating at the same flow rate) or conversely, one could operate with the same initial membrane area but increase the feed flow rate to achieve higher throughput. It should also be possible to significantly increase the selectivity for HPCMP by adjusting solution pH and ionic strength and by using electrically charged membranes. The process optimization diagrams presented herein can provide a framework for analysis of these phenomena in the context of developing embodiments of our HPCMP processes for the purification of biotherapeutics and natural protein products.

Second Set of Experiments—Exemplary Process for Increasing Pore Size

We further explored the capabilities of HPCMP separations by developing a chemical treatment strategy that can be utilized for designing or implementing an embodiment of HPCMP to provide an increase in the average pore size of hollow fiber membranes to enable targeted separations of larger biomolecules. The effectiveness of the chemical treatment can be evaluated using the dextran characterization techniques we developed. Protein separations in a second set of experiments were then performed using an IgG-BSA system to highlight the impact a narrow pore size distribution can have on the selectivity of the membrane(s) of the HPCMP module(s). To further increase the effectiveness and selectivity of the HPCMP separations, limited experiments were performed at different pH and ionic strength to exploit differences in surface charge of the proteins of interest in the second set of experiments. These results were surprisingly found to highlight the fact that the selectivity of the system can be strongly affected by electrostatic interactions in addition to the size-based mechanisms. The results presented below provide further insights into our newly developed HPCMP technique and its viability/effectiveness for protein separations.

All experiments in this second set of experiments were performed using Purema™ H hollow fiber dialyzers from 3M Company (St. Paul, MN) containing 13,200 fibers made from a blend of polyethersulfone (PES) and polyvinylpyrrolidone (PVP). The fibers have an inner diameter of 200 μm, wall thickness of approximately 30 μm, and active length of 23.3 cm, giving a surface area of 1.9 m².

Hypochlorite solutions were prepared by diluting CANI CP-722 industrial bleach (Blue Bell, PA) with deionized water (DI) from a Millipore Direct-Q water purification system (Burlington, MA) to achieve a 4 k ppm hypochlorite solution.

Figure 13:
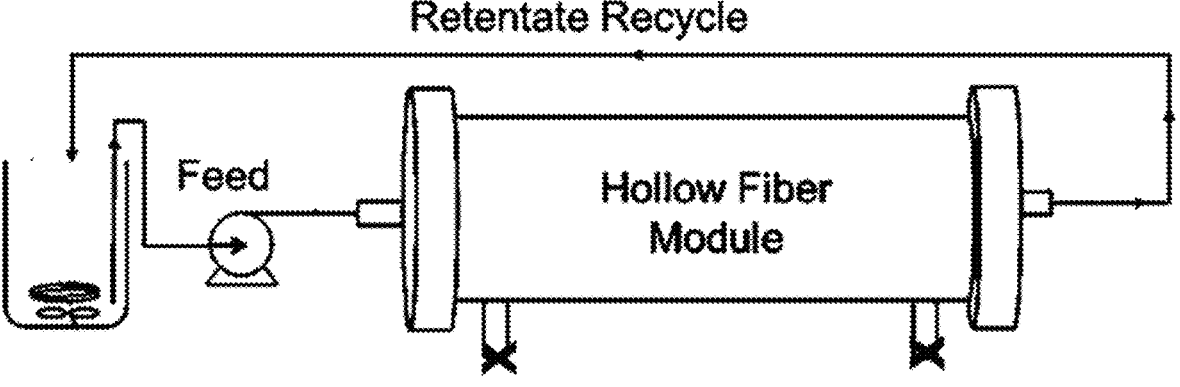
FIG. 13 is schematic view of an exemplary embodiment of a HPCMP module utilized in experiments.
Figure 15:
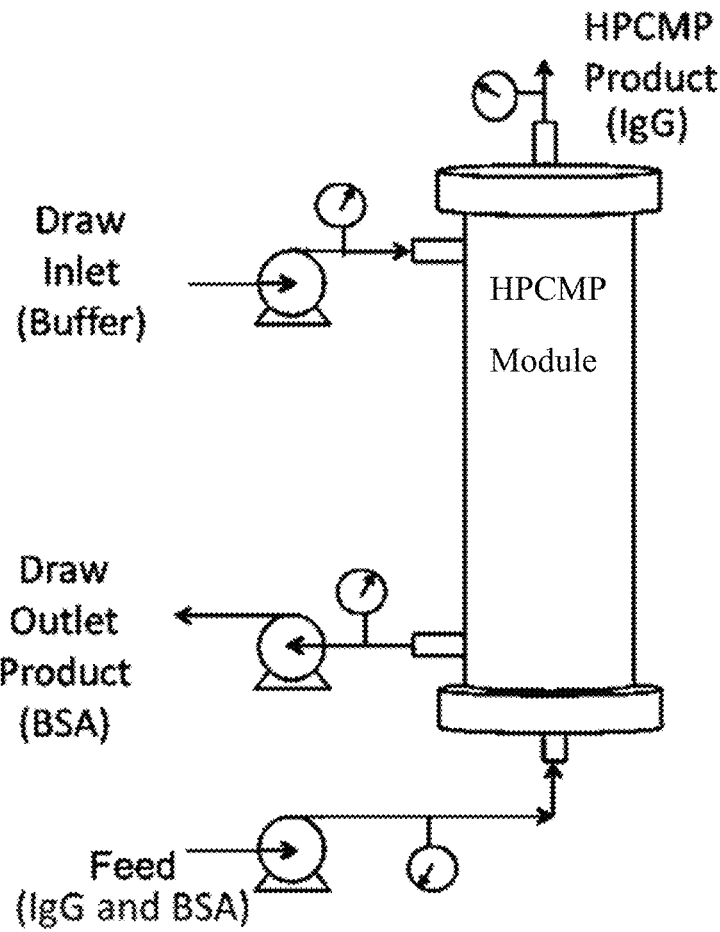
FIG. 15 is a schematic view of an exemplary embodiment of the HPCMP system configured for continuous counter-current operation for protein separations.

The hollow fiber modules were initially wetted by introducing DI water to both bottom ports of the module to remove air and then a permeability test was performed. After the permeability test, both shell side ports are capped and the hypochlorite solution is introduced at room temperature ($21\pm2°$ C.) into the bottom port on the lumen side of the module at 300 ml/min. The system is operated in full recycle mode for 10 minutes with the retentate exit solution being reintroduced into the stirred feed solution (FIG. 13). After 10 minutes, all ports were capped and the hypochlorite-filled dialyzers were placed in a preheated VWR 1350 FD convection oven (S. Plainfield, NJ) at 50° C. for a specified period of time. Afterwards, the dialyzers were removed from the convection oven and immediately flushed with DI water for 30 minutes operating in a countercurrent operation as seen in FIG. 15 to assure complete removal of the hypochlorite solution. The feed and permeate flow rates were operated between 150 and 250 ml/min, respectively. Modification times outlined below only account for the time the modules spent in the oven and not the initial introduction of the hypochlorite solution nor the post-oven flushing. A permeability test was then performed as an initial test on post modification hollow fiber stability. All permeability tests were within 20% of the measured permeability of an unmodified module.

Figure 14:
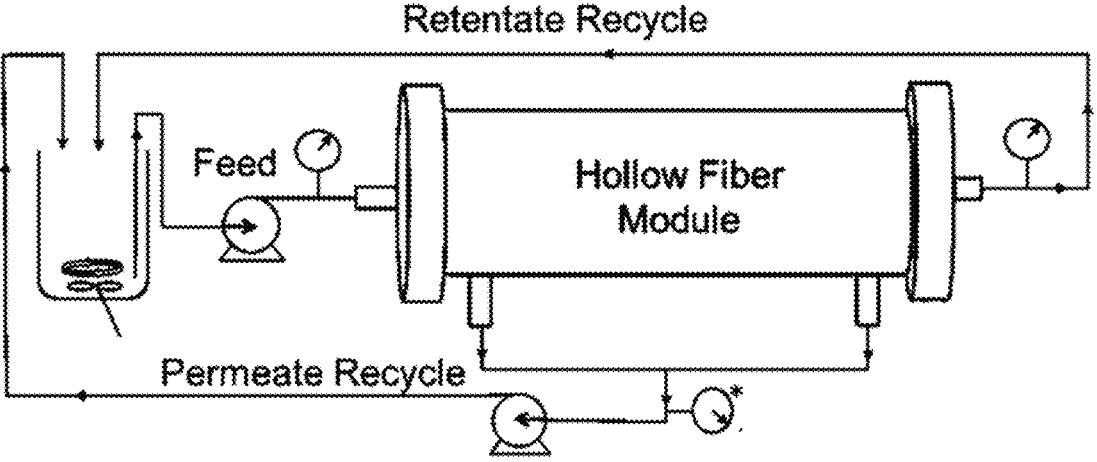
FIG. 14 is schematic view of an exemplary setup of an exemplary HPCMP system used in experiments.

After the post-modification permeability tests, the modules were then flushed with 1×PBS buffer at a pH of 7.2-7.4 and then challenged with a cocktail dextran solution following the new characterization protocols and guidelines as outlined in detail by Yehl and Zydney (2020) to evaluate the sieving characteristics of the newly modified modules. The modules were then operated in a full recycle ultrafiltration setup (FIG. 14) and were challenged with a "cocktail" dextran solution in 1×PBS buffer containing a mixture of several different MW dextrans: 0.2 g/L of Dextran T10 (9-11 kDa), 0.2 g/L of Dextran T40 (35-45 kDa), 0.8 g/L of Dextran T150 (150 kDa), and 1.8 g/L of Dextran T2000 (2000 kDa), all obtained from Sigma-Aldrich (St. Louis, MO).

Data were obtained in total recycle mode, with both the retentate and permeate exit lines recycled back to the stirred feed reservoir to maintain a constant feed concentration throughout the experiment. Feed and permeate flow rates were controlled using two Masterflex L/S peristaltic pumps (Cole-Parmer, Vernon Hill, IL.) fitted with platinum-cured silicone tubing (Cole-Parmer). The pumps were calibrated before each experiment by timed collection using a digital balance. Pressures were monitored throughout the experiments using digital pressure gauges (Ashcroft, Stratford, CT) located immediately before and after the inlet/outlet ports with samples taken from the feed reservoir and permeate/retentate lines after the system had stabilized.

Dextran concentrations were evaluated using an Agilent 1260 infinity II HPLC system (Agilent Scientific instruments, Santa Clara, CA) based on refractive index (RI) measurements. The system used a 3-column setup with the Ultrahydrogel 2000, 500 and 120 columns in series (Waters Corp, Milford, MA), and a guard column placed immediately before the Ultrahydrogel 2000. The HPLC was operated at a constant flow rate of 0.6 ml/min, with the column temperature maintained at 30° C. Samples were injected every 60 minutes. Calibration curves were constructed using EasiVial polyethylene glycol (PEG) calibration standards (Agilent Scientific instruments).

Initial experiments of the second set of experiments were performed with immunoglobulin G (IgG, MW=150 kDa) and bovine serum albumin (BSA, MW=66 kDa), obtained from Novabiologics and Sigma-Aldrich. Feed solutions were prepared by dissolving the proteins in 1×PBS or acetate buffer (Thermo Scientific, Waltham, MA and as well as others, respectively). Protein concentrations were at 2 g/L (unless otherwise stated) for each protein used in the feed solution. The PBS and acetate buffers were prepared from concentrated solutions that were diluted with DI water to a target ionic strength. The solution pH was also adjusted by using a solution of 1-5 M of hydrochloric acid to a target value depending on the experiment. Sodium azide was added at 0.02% w/v to prevent microbial growth during long experimental runs. All solutions were pre-filtered through 0.2 m polyvinylidene fluoride (PVDF) membranes prior to use to remove undissolved protein aggregates.

All separation experiments were setup and shown schematically in FIG. 15 and were run under conditions similar to the first set of experiments discussed above. The experiments were performed using the modified 3M dialyzers (Purema™ H) mounted in a vertical orientation with the feed solution introduced into the lumen side inlet at the bottom. A buffer solution was introduced into the top port on the shell side of the module to achieve countercurrent flow. The draw inlet and outlet flows were controlled using a single pump fitted with two pump-heads to minimize convective flow across the membrane. A separate pump was used to control the feed inlet.

All experiments for the second set of experiments were performed at room temperature (21±2° C.) without any external temperature control. Samples were taken periodically from the feed solution and draw and retentate exits for offline evaluation of the protein concentrations. Protein concentrations and sieving data were evaluated using an Agilent 1260 Infinity II HPLC system (Agilent Scientific instruments, Santa Clara, CA). The HPLC was operated at a constant flow rate of 0.2 mL/min, with the column temperature maintained at 30° C. A Superdex® 200 10/300 GL column (Millipore Sigma) was used for the evaluation. The elution buffer typically matched the experimental buffer used but at experiments with samples at lower pH, 1×PBS buffer with pH 7.2 was used. The absorbance of the protein was measured at 280 nm using the UV-VIS detector for the Agilent system. The results were validated by analyzing the RI detector data as well.

Figure 16:
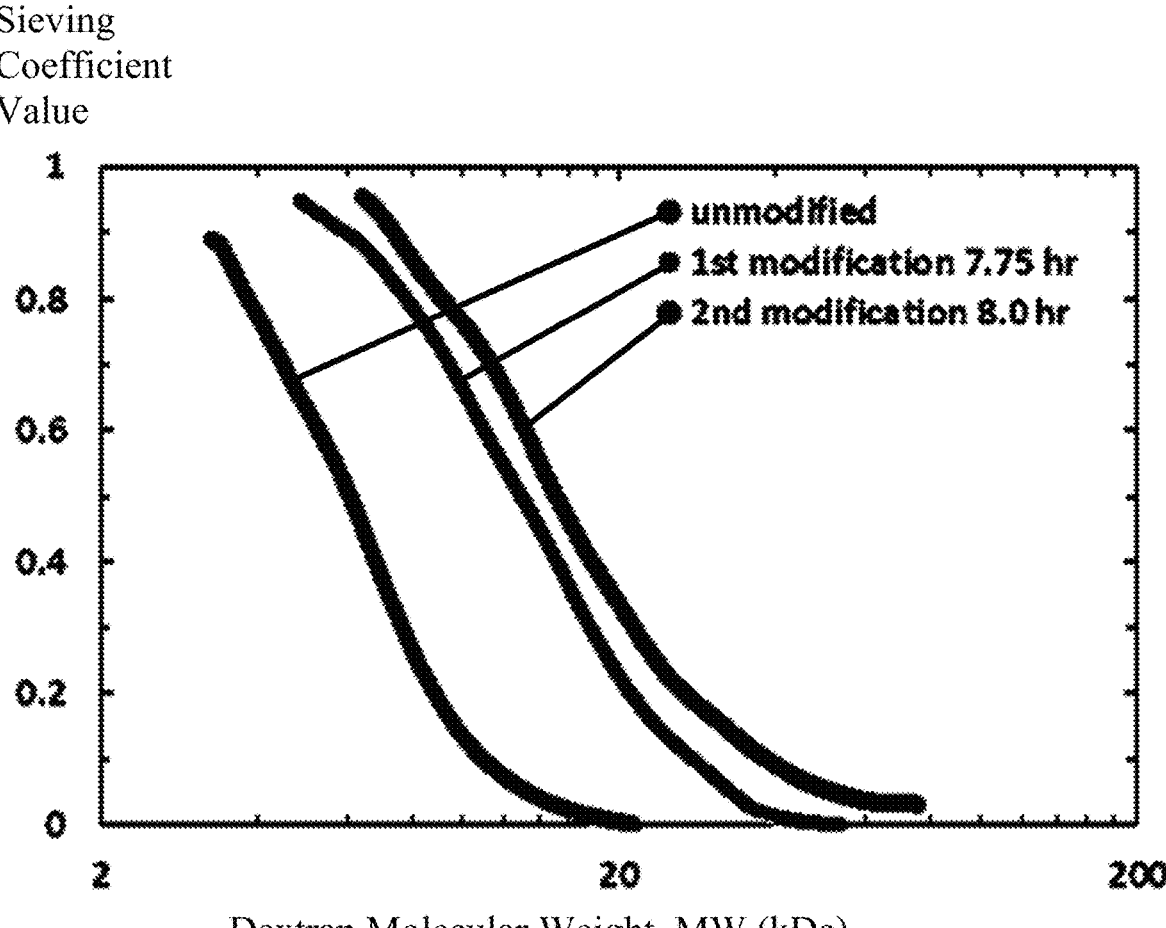
FIG. 16 is a graph illustrating multiple curves with distinct behaviors showing the increasing molecular weight cut off (MWCO) classification as modification time increases.

Dextran characterization tests were performed to see the extent of the hypochlorite modification on the membranes. An unmodified membrane was challenged with polydisperse dextran to serve as a baseline and to show how the transport properties changed over modification time. Modification tests were then performed on the membrane, followed by permeability and characterization testing. FIG. 16 shows the dextran sieving curves for the membranes at various modification times, where:

$$S_o = \frac{C_{Permeate}}{C_{Feed}} \tag{34}$$

FIG. 16 shows three curves with distinct behaviors as well as increasing MWCO classification as modification time increases. Typical classification of an ultrafiltration membrane, in terms of the observed MWCO, is when there is 90% retention of a molecule ($S_o$=0.1). As modification time increases from t=0 to t=7.75 and 8, The observed MWCO shifts from 10→30→40 kDa, respectively. This four-fold increase can be seen above.

Figure 17:
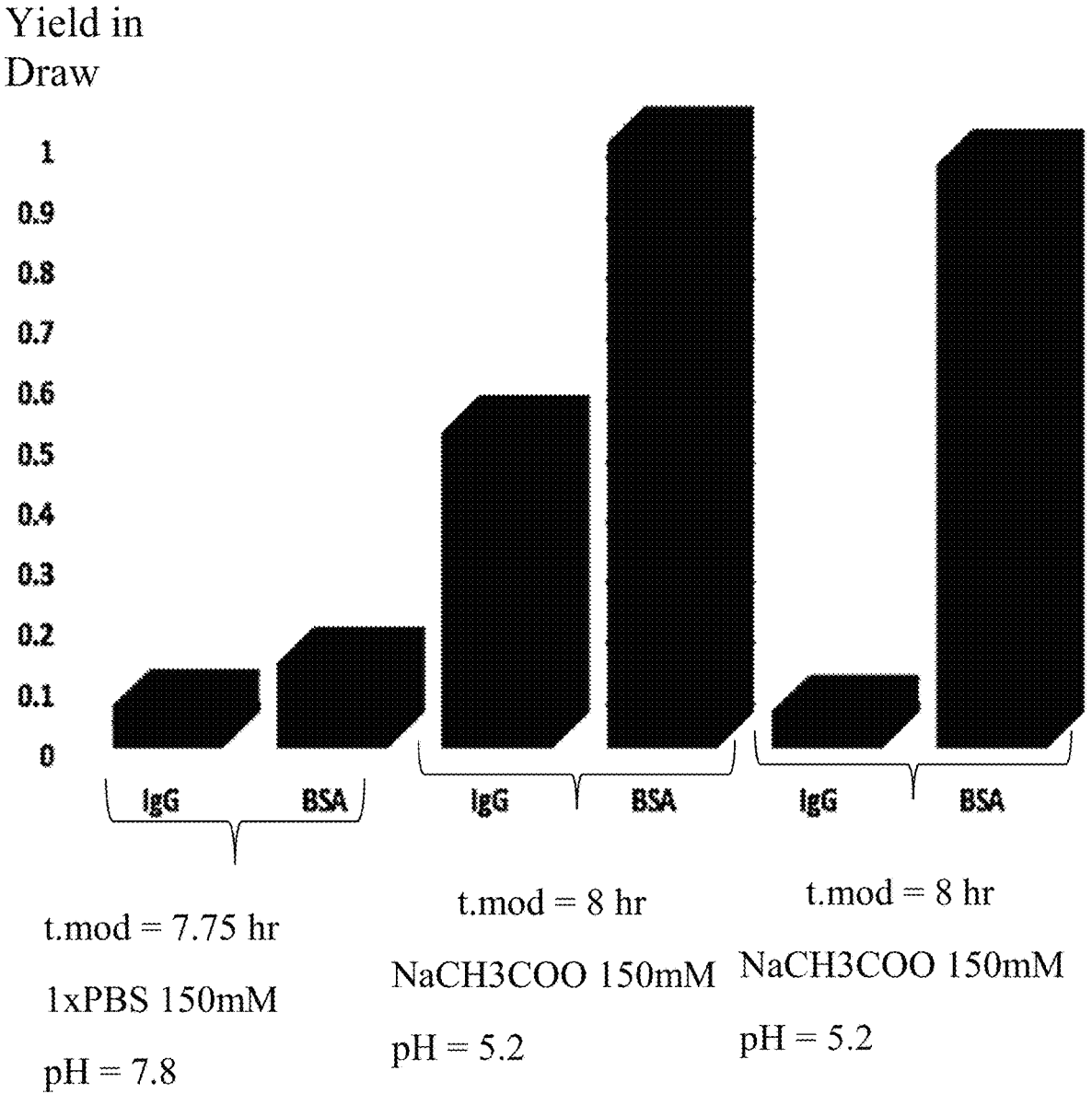
FIG. 17 is a graph illustrating HPCMP experimental results showing yield of Immunoglobulin G (IgG) and bovine serum albumin (BSA) in the draw solution of the conducted experiments.
Figure 18:
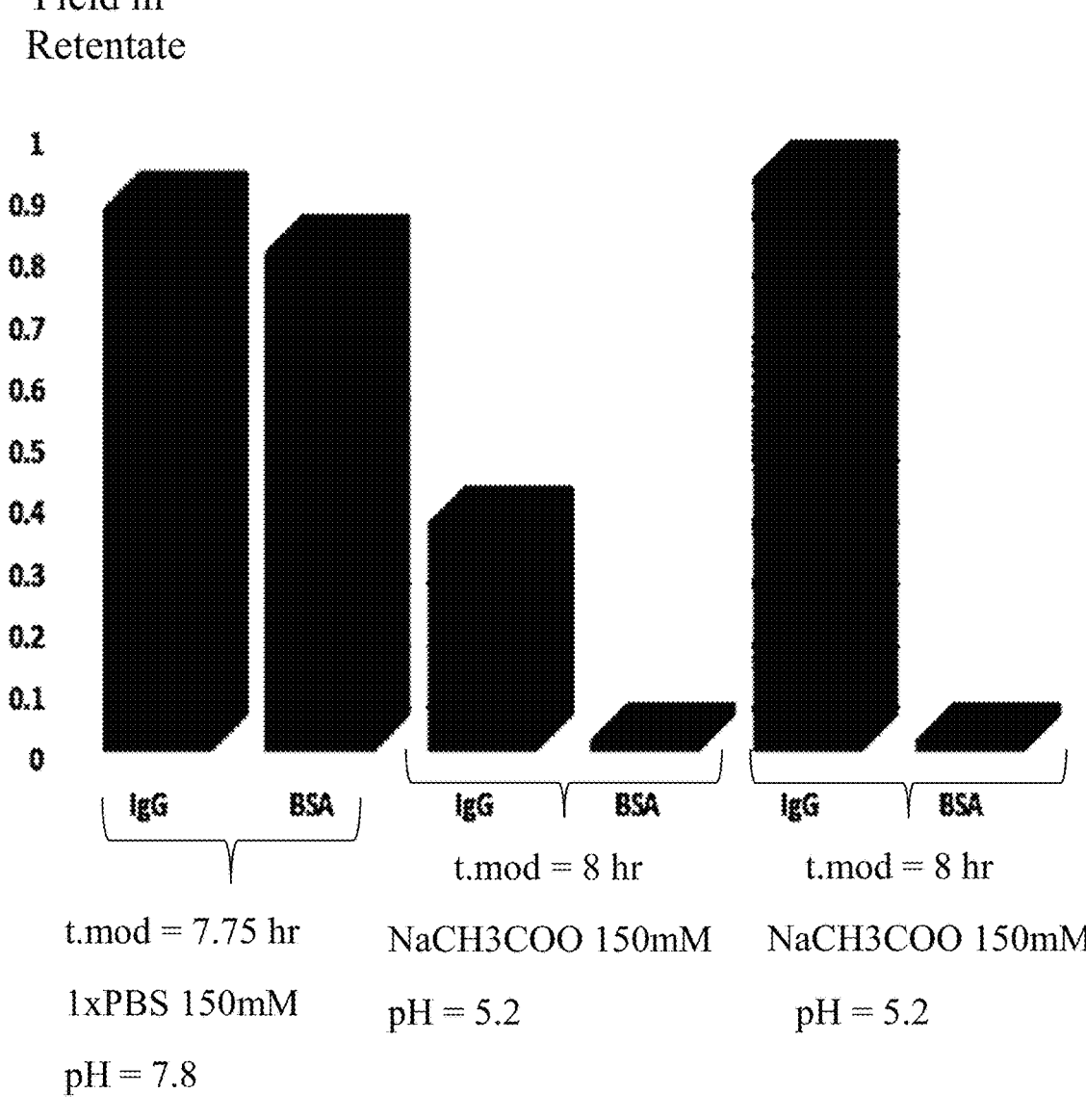
FIG. 18 is a graph illustrating HPCMP experimental results showing yield of IgG and BSA in the retentate solution of the conducted experiments.

FIGS. 17-18 show the separation potential of IgG and BSA in three separate experiments of the second set of experiments when operating under HPCMP conditions. Operating time was 36 hours for each experiment. Flow rates were 0.25±0.03 mL/min and 1.0±0.1 mL/min for the feed and draw solutions, respectively, giving an alpha value of α=4. Operating pressures stayed around 5 kPa throughout all experiments with no detectable change. For the 1$^{st}$ experiment at modification time of t=7.75 hr, with feed and draw solutions being composed of 150 mM PBS buffer at pH=7.8, there is minimal transmission of protein across the membrane, with IgG yield in the draw solution being $Y_{IgG}$<10% and $Y_{BSA}$=12%. With the ionic strength remaining the same, a second experiment was performed (not shown), which shows the yield under more acidic conditions when the pH is changed from 7.8 to 5.2. The yield for BSA in the draw increases almost 7-fold, to $Y_{BSA}$=0.70, with no detectable transmission of IgG in the draw. A 15-minute modification step was then performed to increase the pore size slightly to allow for more transmission of BSA across the membrane into the draw (sieving curve between t=7.75 and 8 hr modified module shown in FIG. 16 above).

Another HPCMP experiment of the second set of experiments conducted under the same aforementioned conditions (see FIGS. 17-18), was performed with the newly modified module. BSA yield increases from 0.70→0.997 but this extra modification time also increased the transmission of IgG across the membrane as well. As a side note, the pH was chosen to more closely match the isoelectric point (pI) of BSA (pI$_{BSA}$=4.5-4.8). When the pH equals the isoelectric point of a molecule, the charge becomes neutral. A more neutrally charged molecule will help facilitate its diffusive transport across the membrane. The buffer range of PBS is pH 5.8 to 7.4, slightly outside the target pH of 5.2, thus sodium acetate buffer with a range of 3.6 to 5.6 was used. To reduce the transmission of IgG across the membrane, a new experiment was performed (see FIGS. 17-18) in which the ionic strength of the sodium acetate buffer is decreased from 150 mM to 10 mM. IgG transmission is minimized as compared to the previous experiment with IgG yield in the draw solution decreasing from $Y_{IgG}$=0.52→0.06, while maintaining similar BSA yield of $Y_{BSA}$=0.96. This corresponds to a yield in the retentate of $Y_{IgG}$≈0.93 and $Y_{BSA}$=0.02 and a purification factor of P≈60.

The above study using the second set of experiments not only provided novel modification techniques to increase the pore size of commercially available membranes, but also explored the effects that buffer conditions such as ionic strength and pH had on the separation of two model proteins of similar size. The tailored HPCMP system utilized in the second set of experiments was used to separate BSA and IgG, achieving greater than 90% yield of both proteins with purification factors greater than 50-fold with significant room for further improvements. Stable operation was again achieved for 96 hours without any evidence of membrane fouling due to the absence of any significant pressure-driven flow. These results further demonstrate the feasibility of using HPCMP for high resolution protein separations and the surprising and unexpected results that can be provided by embodiments of HPCMP, which can provide unexpectedly significant improvements over other conventional protein separation systems (e.g. HPTFF).

As can be appreciated from the above discussed sets of different experiments and modeling, embodiments of HPCMP can provide significant improvement in biomolecule separations while also permitting operations to be conducted to utilize significantly less buffer material to facilitate the separation, e.g., a 2.5-fold reduction (40% less) in buffer compared to HPTFF separations. Moreover, embodiments were surprisingly found to be able to permit highly purified product outlet flows, e.g., with purification factors greater than 50-fold and in some cases greater than 200-fold and yields greater than 99% depending on operating conditions, to be provided while using conventional, single use hollow fiber membranes.

As can be appreciated from the above, embodiments of our high performance countercurrent membrane purification (HPCMP) system and method of HPCMP can be adapted to meet a particular set of design criteria. For instance, the particular type of membrane can be adjusted (e.g. structure, pore size, composition, etc.) to meet a particular set of design criteria. In some embodiments, the feed can include an adeno associated virus (AAV) for separation from one or more host cell proteins, separation of a vaccine from host cell protein(s), or other type of feed. In such embodiments, the separation can produce a purified virus or vaccine from the initial feed mixture.

As another example, it is contemplated that a particular feature described, either individually or as part of an embodiment, can be combined with other individually described features, or parts of other embodiments. The elements and acts of the various embodiments described herein can therefore be combined to provide further embodiments. Thus, while certain present preferred embodiments of our high performance countercurrent membrane purification (HPCMP) system and method as well as embodiments of methods for making and using the same have been shown and described above, it is to be distinctly understood that the invention is not limited thereto but may be otherwise variously embodied and practiced within the scope of the following claims.

What is claimed is:

1. A method of separating proteins comprising:
    passing a feed to a High Performance Countercurrent Membrane Purification (HPCMP) module having at least one membrane within a vessel, the feed comprising a first protein and a second protein, the feed passed through the HPCMP module in countercurrent flow with a buffer fed to the vessel of the HPCMP module;
    separating the first protein from the second protein via differences in diffusive flux across the at least one membrane of the HPCMP module;
    outputting a product flow and a buffer outlet flow from the vessel of the HPCMP module, the product flow having a purity of the first protein that is greater than the purity of the first protein within the feed, the buffer outlet flow having a purity of the second protein that is greater than the purity of the second protein within the feed passed to the HPCMP module;
    wherein the passing of the feed and the outputting of the product flow and the buffer outlet flow occur simultaneously during a continuous flow operation of the HPCMP module.

2. The method of claim 1, wherein the at least one membrane is a single use membrane.

3. The method of claim 1, wherein the at least one membrane is a hollow fiber membrane.

4. The method of claim 1, wherein the purity of the first protein within the product flow is at least fifty times higher than the purity of the first protein within the feed.

5. The method of claim 1, wherein the purity of the second protein within the buffer outlet flow is at least fifty times higher than the purity of the second protein within the feed.

6. The method of claim 1, wherein the purity of the first protein within the product flow is at least 100 times higher than the purity of the first protein within the feed and the purity of the second protein within the buffer outlet flow is at least 100 times higher than the purity of the second protein within the feed.

7. The method of claim 1, wherein the feed is a liquid flow and the buffer is a liquid, the product flow is a liquid and the buffer outlet flow is a liquid.

8. The method of claim 1, comprising:
    outputting the feed from a bioreactor upstream of the HPCMP module;

passing the feed through at least one of ultrafiltration (UF) and dialysis upstream of the HPCMP module.

9. The method of claim 8, wherein the dialysis is countercurrent dialysis (CCD).

10. The method of claim 8, comprising:

passing the buffer through at least one of ultrafiltration (UF) and dialysis before the buffer is fed to the HPCMP module.

11. The method of claim 10, wherein the dialysis is countercurrent dialysis (CCD).

12. The method of claim 1, comprising:

controlling at least one of ionic strength of the feed and pH of the feed to increase selectivity.

13. The method of claim 1, comprising:

adjusting at least one of ionic strength of the buffer and pH of the buffer during the continuous operation of the HPCMP module to increase selectivity.

14. The method of claim 1 in which the at least one membrane is pretreated to increase an effective pore size of the at least one membrane.

15. The method of claim 1, wherein the first protein is a monoclonal antibody, bovine serum albumin (BSA), myoglobin (Mb), or Immunoglobulin G (IgG); and the second protein is a protein within a mixture of host cell proteins, BSA, Mb, or IgG.

16. A method of separating biological material comprising:

passing a feed to a High Performance Countercurrent Membrane Purification (HPCMP) module having at least one membrane within a vessel, the feed comprising a first desired biological product and at least one second component, the feed passed through the HPCMP module in countercurrent flow with a buffer fed to the vessel of the HPCMP module;

separating the first desired biological product from the second component via differences in diffusive flux across the at least one membrane of the HPCMP module; and outputting a product flow and a buffer outlet flow from the vessel of the HPCMP module, the product flow having a purity of the first desired biological product that is greater than the purity of the first desired biological product within the feed, the buffer outlet flow having a purity of the at least one second component that is greater than the purity of the at least one second component within the feed passed to the HPCMP module;

wherein the passing of the feed and the outputting of the product flow and the buffer outlet flow occur simultaneously during a continuous flow operation of the HPCMP module.

17. The method of claim 16, wherein the purity of the first desired biological product within the product flow is at least fifty times higher than the purity of the first desired biological product within the feed.

18. The method of claim 16, wherein the purity of the at least one second component within the buffer outlet flow is at least fifty times higher than the purity of the least one second component within the feed.

19. The method of claim 16, wherein the purity of the first desired biological product within the product flow is at least 100 times higher than the purity of the first desired biological product within the feed and the purity of the at least one second component within the buffer outlet flow is at least 100 times higher than the purity of the at least one second component within the feed.

20. The method of claim 16, wherein the first desired biological product is a pegylated protein, a glycoconjugate vaccine, a monoclonal antibody, bovine serum albumin (BSA), myoglobin (Mb), Immunoglobulin G (IgG) or an antibody drug conjugate; and the at least one second component is unreacted polyethylene glycol, polysaccharide, or drug molecule or is a protein within a mixture of host cell proteins, BSA, Mb, or IgG.

21. The method of claim 20, wherein the first desired biological product is the monoclonal antibody, the bovine serum albumin (BSA), the myoglobin (Mb), or the Immunoglobulin G (IgG); and the at least one second component is the protein within the mixture of host cell proteins, BSA, Mb, or IgG.

* * * * *